United States Patent
Ojha et al.

(10) Patent No.: US 9,249,398 B2
(45) Date of Patent: Feb. 2, 2016

(54) USE OF MYCOBACTERIUM SMEGMATIS TREHALOSE DIMYCOLATE HYDROLASE

(71) Applicant: University of Pittsburgh-Of the Commonwealth System of Higher Education, Pittsburgh, PA (US)

(72) Inventors: Anil Kumar Ojha, Sewickley, PA (US); Yong Yang, Pittsburgh, PA (US); Peijun Zhang, Pittsburgh, PA (US)

(73) Assignee: University of Pittsburgh-Of the Commonwealth System of Higher Education, Pittsburgh, PA (US)

( * ) Notice: Subject to any disclaimer, the term of this patent is extended or adjusted under 35 U.S.C. 154(b) by 65 days.

(21) Appl. No.: 13/904,821

(22) Filed: May 29, 2013

(65) Prior Publication Data

US 2013/0323224 A1    Dec. 5, 2013

Related U.S. Application Data

(60) Provisional application No. 61/653,334, filed on May 30, 2012.

(51) Int. Cl.
| | | |
|---|---|---|
| *A61K 38/46* | (2006.01) | |
| *C12N 9/24* | (2006.01) | |
| *C12N 9/18* | (2006.01) | |

(52) U.S. Cl.
CPC .............. *C12N 9/24* (2013.01); *A61K 38/465* (2013.01); *C12N 9/18* (2013.01)

(58) Field of Classification Search
CPC ........... A61K 38/465; C12N 9/18; C12N 9/24
See application file for complete search history.

(56) References Cited

PUBLICATIONS

Branden et al., Introduction to Protein Structure, Garland Publishing Inc., New York, p. 247, 1991.*
Witkowski et al., Biochemistry 38:11643-11650, 1999.*
Seffernick et al., J. Bacteriol. 183(8):2405-2410, 2001.*
El-Hajj et al., Journal of Clinical Microbiology 39(11):4131-4137, 2001.*
Bhatti, Optimization of rTDMH as a Reagent Toward Improving the Sensitivity of the RT-PCR Based Diagnosis for Mycobacterium Tuberculosis, *Thesis for the University of Pittsburgh* 69 pages (Dec. 1, 2011).
Gil et al., "Mycobacteriophage Ms6 LysB Specifically Targets the Outer Membrane of *Mycobacterium smegmatis*," Microbiology 156:1497-1504 (2010).
Ojha et al., "Enzymatic Hydrolysis of Trehalose Dimycolate Releases Free Mycolic Acids during Mycobacterial Growth in Biofilms," *Journal of Biological Chemistry* 285(23): 17380-17389 (Jun. 4, 2010).
Ojha et al., "Growth of *Mycobacterium tuberculosis* Biofilms Containing Free Mycolic Acids and Harbouring Drug-tolerant Bacteria," *Molecular Microbiology* 69(1):164-174 (May 27, 2008).

* cited by examiner

*Primary Examiner* — Delia Ramirez
(74) *Attorney, Agent, or Firm* — Klarquist Sparkman, LLP

(57) ABSTRACT

Methods are disclosed herein for treating an infection with a *Mycobacterium* infection. Methods are also disclosed for treating a *Mycobacterium* biofilm. The method include the use of trehalose dimycolate hydrolase, a variant thereof, or a nucleic acid encoding trehalose dimycolate hydrolase or a variant thereof Methods are also disclosed for detecting a *Mycobacterium* in a sample from a subject. The methods include treating the sample with trehalose dimycolate hydrolase or a variant thereof, and detecting a *Mycobacterium* nucleic acid in the sample.

18 Claims, 12 Drawing Sheets

FIG. 2A
FIG. 2B
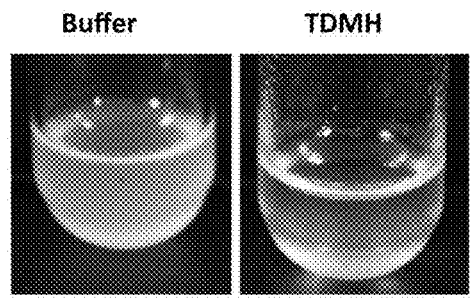
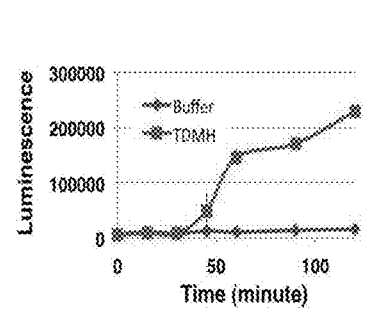
FIG. 2C
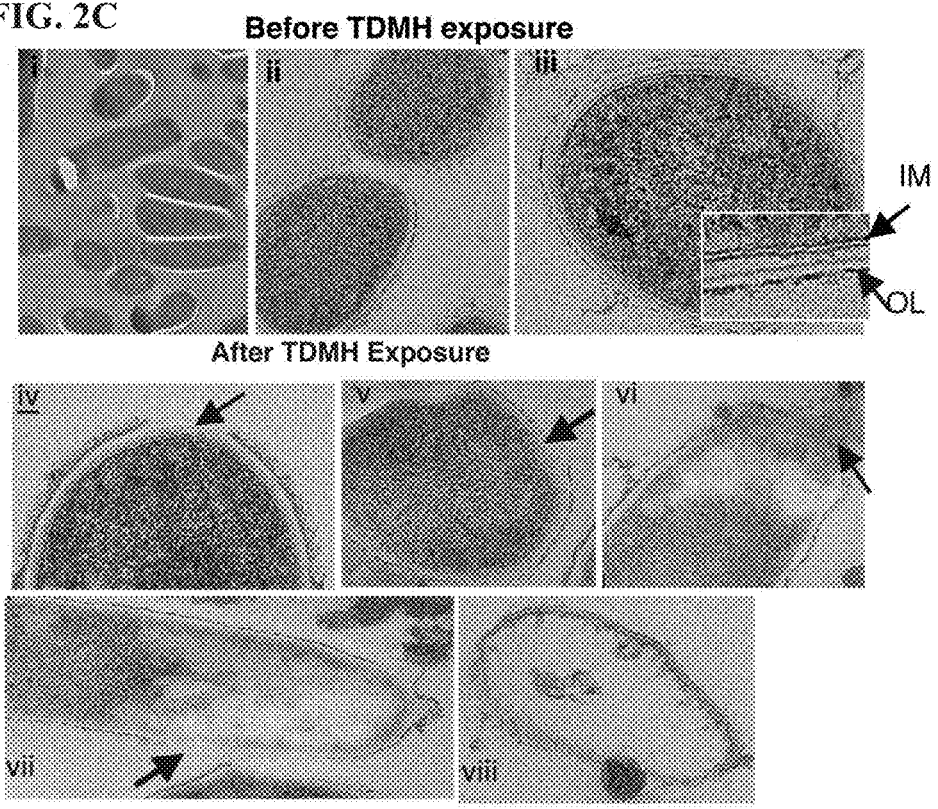
FIG. 2D
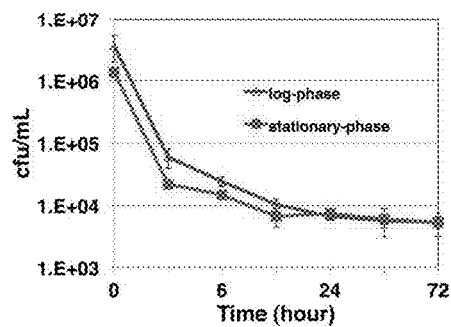

US 9,249,398 B2

USE OF MYCOBACTERIUM SMEGMATIS TREHALOSE DIMYCOLATE HYDROLASE

PRIORITY CLAIM

This claims the benefit of U.S. Provisional Application No. 61/653,334, filed May 30, 2012, which is incorporated by reference herein.

STATEMENT OF GOVERNMENT SUPPORT

This invention was made with government support under grant no. AI079288 awarded by the National Institutes of Health. The government has certain rights in the invention.

FIELD

This related to the fields of diagnosis and treatment, specifically to the detection and treatment of *Mycobacterium* infections.

BACKGROUND

*Mycobacteria* are a genus of aerobic intracellular bacterial organisms that, upon infection of a host, survive within endosomal compartments of monocytes and macrophages. Human mycobacterial diseases include tuberculosis (caused by *M. tuberculosis*), leprosy (caused by *M. leprae*), Bairnsdale ulcers (caused by *M. ulcerans*), and various infections caused by *M. marinum, M. kansasii, M. scrofulaceum, M. szulgai, M. xenopi, M. fortuitum, M. chelonei, M. haemophilum* and *M. intracellulare* (see Wolinsky, E., Chapter 37 in Microbiology: Including Immunology and Molecular Genetics, 3rd Ed., Harper & Row, Philadelphia, 1980).

One third of the world's population harbors *M. tuberculosis* and is at risk for developing tuberculosis (TB). In immunocompromised patients, tuberculosis is increasing at a nearly logarithmic rate, and multidrug resistant strains are appearing. In addition, Mycobacterial strains which were previously considered to be nonpathogenic strains (e.g., *M. avium*) have now become major killers of immunosuppressed AIDS patients. Moreover, current Mycobacterial vaccines are either inadequate (such as the BCG vaccine for *M. tuberculosis*) or unavailable (such as for *M. leprae*) (Kaufmann, S., *Microbiol. Sci.* 4:324-328, 1987; U.S. Congress, Office of Technology Assessment, The Continuing Challenge of Tuberculosis, pp. 62-67, OTA-H-574, U.S. Government Printing Office, Washington, D.C., 1993).

The most distinctive cellular component of *M. tuberculosis* is its structurally atypical, functionally diverse, and physically robust cell envelope, which is widely held as an important contributor to the characteristic resilience of the pathogen (see, for example, Ehrt and Schnappinger, *Cell Microbiol* 11, 1170, 2009; Vandal et al., *J Bacteriol* 191, 625, 2009; Chatterjee, *Curr Opin Chem Biol* 1, 579, 1997; Brennan and Nikaido, *Annu Rev Biochem* 64, 29, 1995). The thick and waxy envelope presumably serves as physical barrier against antimycobacterial agents including antibiotics, as well as poses significant challenges in gaining physical access to its intracellular content for research and diagnostic purposes. There exists a need to identify an agent that could specifically recognize and destabilize *M. tuberculosis* cell envelope structure, such as to cause rapid but specific lysis of the pathogen. In addition, a need remains for methods for effective methods of detecting and treating a *Mycobacterium* infection, or for treating biofilms that contain the *Mycobacterium*, such as biofilms on indwelling medical devices.

SUMMARY

Methods are disclosed herein for treating an infection with a *Mycobacterium* infection. Methods are also disclosed for treating a *Mycobacterium* biofilm. The methods include the use of trehalose dimycolate hydrolase (TDMH), a variant thereof, or a nucleic acid encoding trehalose dimycolate hydrolase (TDMH) or a variant thereof.

In additional embodiments, methods are disclosed for detecting a *Mycobacterium*, such as *M. tuberculosis*. The methods include contacting a sample from the subject with an effective amount of a trehalose dimycolate hydrolase (TDMH), or a variant thereof, and detecting *Mycobacterium* nucleic acids. In some embodiments, the methods include the use of polymerase chain reaction to amplify the *Mycobacterium* nucleic acid. In additional embodiments, the sample is a sputum sample.

The foregoing and other features and advantages will become more apparent from the following detailed description of several embodiments, which proceeds with reference to the accompanying figures.

BRIEF DESCRIPTION OF THE FIGURES

FIGS. 2A-2D. TDMH-exposure causes lysis of *M. tuberculosis*. A. Clearance of *M. tuberculosis* (H37Rv) suspension ($10^8$ cfu/mL) after 48 hours in PBST containing 8 µM of TDMH. In the control, an equal volume of storage buffer was added in the cell suspension. B. Luciferine-luciferase based measurement of ATP released in an *M. tuberculosis* (mc²7000) suspension ($10^8$ cfu/mL) exposed to 8 µM TDMH (also see FIG. 9). The error bars represent the standard error of three independent experiments. As a negative control ATP was measured in culture exposed to storage buffer. C. Freeze substitution electron microscopy of $10^9$ cfu/mL of *M. tuberculosis* (mc²7000) before (i-iii), and after 12-hour exposure to 8 µM TDMH (iv-viii). Digital images in i-iii are independent fields showing low magnification of intact cells (i), and high magnification of their cross sections before TDMH exposure. A close-up view of the envelope layers is shown in the inset of image iii. The cell inner membrane and outer layer are marked as IM and OL. Digital images in iv-viii are independent fields showing various stages of lysing bacilli in a TDMH-exposed population. Cells shown are: (iv) with a lesion in the outer layer (marked with arrow head); (v) with a distorted cytoplasm, presumably moments before the cytoplasm ejection due to the membrane lesion; (vi and vii) in the act of releasing cytoplasmic contents and; (viii) completely devoid of cytoplasm. Arrows point to the lesion sites. D. Exposure of log-phase (7-day old with OD 0.5) and stationary phase (35-day old with OD 3.0) cultures of H37Rv to 8 µM TDMH.

FIG. 11A shows the ratio of TDM to FM in samples shown in FIG. 3A. Ratios were determined by the densitometric analysis of the two lipids for every time point using ImageJ. B. Relative amount of TMM in samples shown in FIG. 38. Values were determined using the O-hour for buffer and TDMH-treated cells as reference. The actual pixel densities of the spots were determined using ImageJ.

SEQUENCE LISTING

Figure 1A:
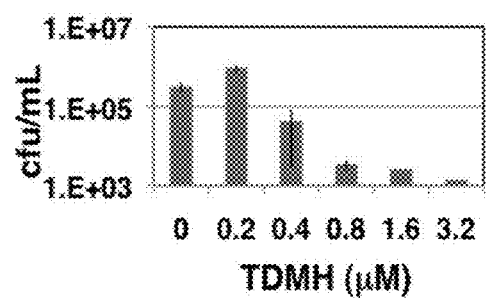
FIGS. 1A-1D. Loss of *M. tuberculosis* viability upon TDMH exposure. A. Viability of $10^6$ cfu/mL of bacilli after exposure to various concentrations of TDMH for 24 hours in PBST. In the control (0 µM) experiment an equivalent volume of storage buffer was used. B. Viability of bacilli after TDMH exposure in growth media of mycobacteria (Sauton's media and 7H9 with and without OADC) and macrophage (DMEM with and without serum). PBST was used as a control. C. Effects of equivalent concentration of constituent amino acid of Sauton's media (26 mM Asparagine, L-Asn) on the antimycobacterial activity of TDMH in PBST. D. Sauton's media agar plates containing a lawn ($10^6$ cfu/mL) of *M. tuberculosis* bacilli with either storage buffer or 200 µg of TDMH spotted in the center, and incubated for 3 weeks. The error bars in panels A-C represent the standard errors of three independent experiments.

The nucleic and amino acid sequences are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file [8123-87193-03_Sequence_Listing, May 29, 2013, 5.80 KB], which is incorporated by reference herein.

SEQ ID NO: 1 is an exemplary amino acid sequence of TMDH.

SEQ ID NO: 2 is another exemplary amino acid sequence of TMDH. SEQ ID NO: 2 includes five additional amino acids at the N-terminus as compared to SEQ ID NO: 1.

SEQ ID NO: 3 is an exemplary nucleic acid sequence encoding TMDH.

SEQ ID NO: 4 is the amino acid sequence of a peptide linker.

SEQ ID NO: 5 and SEQ ID NO: 6 are the nucleic acid sequences of primers.

SEQ ID NO: 7 is the nucleic acid sequence of a molecular beacon.

DETAILED DESCRIPTION

Current diagnostic tools being used for tuberculosis lack the speed and sensitivity necessary to successfully combat the current tuberculosis epidemic. Methods such as real-time polymerase chain reaction (RT-PCR) can provide the rapid and specific diagnosis that is currently in demand in the global community. Its disadvantage is that due to the waxy and robust nature of the *Mycobacterium* membrane, such as the *M. tuberculosis* membrane, not enough genomic DNA is present to provide for amplification in a RT-PCR.

It is disclosed herein that hydrolysis of one of the abundant glycolipids of mycobacterial envelope, trehalose, 6,6'-dimycolate (TDM), by a recombinant TDM-specific hydrolase (TDMH) caused rapid lysis of *Mycobacterium* cells. This rapid lysis by TDMH was exploited in conjunction with the RT-PCR to develop sensitive methods for the diagnosis of tuberculosis. The results demonstrated that incubation of both attenuated *M. tuberculosis* and virulent *M. tuberculosis* with TDMH resulted in lysis. Detection methods, such as method for detection of nucleic acids (for example, RT-PCR) then can be used for sensitive amplification of the mycobacterial DNA. In some embodiments, methods are provided for detecting a *Mycobacterium* that include contacting a sample with an effective amount of TDMH or a variant thereof.

In other embodiments, the rapid lysis by TDMH can also be used to treat biofilms and can be used therapeutically. The methods include the use of a composition that includes an effective amount of TDMH or a variant thereof.

Terms

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of this disclosure, the following explanations of specific terms are provided:

Administration:

To provide or give a subject an agent, for example, a composition that includes TDMH by any effective route. Exemplary routes of administration include, but are not limited to, oral, injection (such as subcutaneous, intramuscular, intradermal, intraperitoneal, and intravenous), sublingual, transdermal (e.g., topical), intranasal and inhalation routes.

Amplification:

Of a nucleic acid molecule (e.g., a DNA or RNA molecule) refers to use of a technique that increases the number of copies of a nucleic acid molecule in a specimen. An example of amplification is the polymerase chain reaction, in which a biological sample collected from a subject is contacted with a pair of oligonucleotide primers, under conditions that allow for the hybridization of the primers to a nucleic acid template in the sample. The primers are extended under suitable conditions, dissociated from the template, and then re-annealed, extended, and dissociated to amplify the number of copies of the nucleic acid. The product of amplification can be characterized by electrophoresis, restriction endonuclease cleavage patterns, oligonucleotide hybridization or ligation, and/or nucleic acid sequencing using standard techniques. Other examples of amplification include strand displacement amplification, as disclosed in U.S. Pat. No. 5,744,311; transcription-free isothermal amplification, as disclosed in U.S. Pat. No. 6,033,881; repair chain reaction amplification, as disclosed in PCT Application No. WO 90/01069; ligase chain reaction amplification, as disclosed in European Publication No. EP-A-320 308; gap filling ligase chain reaction amplification, as disclosed in U.S. Pat. No. 5,427,930; and NASBA™ RNA transcription-free amplification, as disclosed in U.S. Pat. No. 6,025,134. Several embodiments include multiplex qPCR assays, which are useful for amplifying and detecting multiple nucleic acid sequences.

Animal:

Living multi-cellular vertebrate organisms, a category that includes, for example, mammals and birds. The term mammal includes both human and non-human mammals. Similarly, the term "subject" includes both human and veterinary subjects.

Antibacterial Enzyme:

An enzyme (such as a proteolytic, pore-forming, degradative, or inhibitory enzyme) that kills or damages a bacterial species or particular strain thereof. The enzyme can damage the cell wall of the bacteria, disrupt cell membranes associated with the cell wall or within the bacteria, inhibit protein synthesis within the bacteria, or disrupt the sugar backbone. The enzyme may be a natural, wild-type enzyme, a variant modified by conventional techniques, conjugated to other molecules, recombinantly expressed, or synthetically constructed.

Antibiotic:

A chemical substance, produced by microorganisms, naturally occurring, or synthetically prepared, that has the capacity to inhibit the growth or replication of bacteria. Exemplary antibacterial antibiotics include, but are not limited to, a beta-lactam, a cephalosporin, an aminoglycoside, a sulfonamide, a macrolide, a tetracycline, a silver salt, and the like. Such antibiotics can be either bacteriostatic or bactericidal.

Antimicrobial Agent:

An agent that kills microorganisms or suppresses (or inhibits) their growth or multiplication. This term includes both microbiocidal agents, as well as those agents that inhibit growth or maintain stasis of target microorganisms, such as bacteria (an antibacterial agent), protozoa (an antiprotozoal agent), or fungi (an antifungal agent). An antimicrobial agent includes, but is not limited to, a chemical compound, small molecule, peptide mimetic, peptide, or protein for killing or suppressing their or growth. An agent has "antimicrobial activity" if it can damage a microorganism in such a way that it results in the death of a microorganism or suppresses the growth or multiplication of a microorganism. An antimicrobial activity includes, but is not limited to, microbial cell lysis. In one embodiment, an antimicrobial agent is cytotoxic.

In another embodiment, antimicrobial activity can be measured by the production or the size of a clear zone surrounding a bacterial colony on a microbial lawn, wherein the antimicrobial agent is a diffusible agent released from the bacteria. In one embodiment, an antimicrobial activity is bacterial cell lysis (an antibacterial activity).

Bioassay:

Measurement of the concentration or potency of a substance by its effect on living cells or tissues.

Biofilm:

A mass or community of microorganisms attached to a living or non-living surface (such as a surface of a medical device, a tissue, an organ, a household object), and the associated extracellular substances produced by one or more of the attached microorganisms. The extracellular substances are typically polymeric substances that commonly include a matrix of complex polysaccharides, proteinaceous substances and glycopeptides. The microorganisms in a biofilm may include, but are not limited to, bacteria, fungi and protozoa. In a "bacterial biofilm," the microorganisms include one or more species of bacteria, such as a *Mycobacterium*. The nature of a biofilm, such as its structure and composition, may depend on the particular species of bacteria present in the biofilm. An established bacterial biofilm is a bacterial biofilm that is recalcitrant to antimicrobial or antibacterial treatments that are normally effective at inhibiting or controlling the growth of the corresponding isolated bacteria or planktonic bacteria.

Biological Sample:

A sample of biological material obtained from a subject. Biological samples include all clinical samples useful for detection of disease or infection (e.g., *Mycobacterium* infection) in subjects. Appropriate samples include any conventional biological samples, including clinical samples obtained from a human or veterinary subject. Exemplary samples include, without limitation, cells, cell lysates, blood smears, cytocentrifuge preparations, cytology smears, biological fluids (e.g., blood, plasma, serum, saliva, sputum, urine, bronchoalveolar lavage, semen, cerebrospinal fluid (CSF), etc.), tissue biopsies or autopsies, fine-needle aspirates, and/or tissue sections. In a particular example, a biological sample is obtained from a subject having, suspected of having or at risk of having a *Mycobacterium* infection.

cDNA (Complementary DNA):

A piece of DNA lacking internal, non-coding segments (introns) and regulatory sequences that determine transcription. cDNA is synthesized in the laboratory by reverse transcription from messenger RNA extracted from cells.

Conservative Variants:

"Conservative" amino acid substitutions are those substitutions that do not substantially affect or decrease an activity or antigenicity of the *Mycobacterium* polypeptide. Specific, non-limiting examples of a conservative substitution include the following examples:

| Original Residue | Conservative Substitutions |
| --- | --- |
| Ala | Ser |
| Arg | Lys |
| Asn | Gln, His |
| Asp | Glu |
| Cys | Ser |
| Gln | Asn |
| Glu | Asp |
| His | Asn; Gln |
| Ile | Leu, Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

The term conservative variation also includes the use of a substituted amino acid in place of an unsubstituted parent amino acid, provided that antibodies raised to the substituted polypeptide also immunoreact with the unsubstituted polypeptide, or that an immune response can be generated against the substituted polypeptide that is similar to the immune response against and unsubstituted polypeptide, such a *Mycobacterium* antigen. Thus, in one embodiment, non-conservative substitutions are those that reduce an activity or antigenicity.

Consists Essentially of/Consists of:

With regard to a polypeptide, a polypeptide that consists essentially of a specified amino acid sequence if it does not include any additional amino acid residues. However, the polypeptide can include additional non-peptide components, such as labels (for example, fluorescent, radioactive, or solid particle labels), sugars or lipids. With regard to a polypeptide, a polypeptide that consists of a specified amino acid sequence does not include any additional amino acid residues, nor does it include additional non-peptide components, such as lipids, sugars or labels.

Contacting:

The process of incubating one agent in the presence of another. Thus, when a cell is contacted with an agent, the cell is incubated with the agent for a sufficient period of time for the agent and the cell to interact.

Degenerate Variant:

A polynucleotide encoding an epitope of an *Mycobacterium* polypeptide that includes a sequence that is degenerate as a result of the genetic code. There are 20 natural amino acids, most of which are specified by more than one codon. Therefore, all degenerate nucleotide sequences are included in this disclosure as long as the amino acid sequence of the *Mycobacterium* polypeptide encoded by the nucleotide sequence is unchanged.

Detecting:

To identify the existence, presence, or fact of something. General methods of detecting are known to the skilled artisan and may be supplemented with the protocols and reagents disclosed herein. For example, included herein are methods of detecting a *Mycobacterium* in a biological sample. Detection can include a physical readout, such as fluorescence or a reaction output.

Diagnostic:

Identifying the presence or nature of a pathologic condition, such as, but not limited to, a Mycobactrium infection and/or tuberculosis. Diagnostic methods differ in their sensitivity and specificity. The "sensitivity" of a diagnostic assay is the percentage of diseased individuals who test positive (percent of true positives). The "specificity" of a diagnostic assay is 1 minus the false positive rate, where the false positive rate is defined as the proportion of those without the disease who test positive. While a particular diagnostic method may not provide a definitive diagnosis of a condition, it suffices if the method provides a positive indication that aids in diagnosis. "Prognostic" means predicting the probability of development (for example, severity) of a pathologic condition, such as tuberculosis.

Effective Amount:

The "effective amount" of a composition is the quantity of a composition sufficient to achieve a desired result. For instance, this can be the amount of a composition containing a sufficient dose of a hyrdolase sufficient to inhibit the formation of a bacterial biofilm on a surface of an object. The effective amount of a composition will depend on, for example, the amount of the hydrolase contained in the composition, the concentration of the hydrolase in the composition, the amount of time the composition is in contact with the surface, the temperature at which the interaction between the composition and the surface takes place, and the like.

Expression Control Sequences:

Nucleic acid sequences that regulate the expression of a heterologous nucleic acid sequence to which it is operatively linked. Expression control sequences are operatively linked to a nucleic acid sequence when the expression control sequences control and regulate the transcription and, as appropriate, translation of the nucleic acid sequence. Thus expression control sequences can include appropriate promoters, enhancers, transcription terminators, a start codon (i.e., ATG) in front of a protein-encoding gene, splicing signal for introns, maintenance of the correct reading frame of that gene to permit proper translation of mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter.

A promoter is a minimal sequence sufficient to direct transcription. Also included are those promoter elements which are sufficient to render promoter-dependent gene expression controllable for cell-type specific, tissue-specific, or inducible by external signals or agents; such elements may be located in the 5' or 3' regions of the gene. Both constitutive and inducible promoters are included (see e.g., Bitter et al., *Methods in Enzymology* 153:516-544, 1987). For example, when cloning in bacterial systems, inducible promoters such as pL of bacteriophage lambda, plac, ptrp, ptac (ptrp-lac hybrid promoter) and the like may be used. In one embodiment, when cloning in mammalian cell systems, promoters derived from the genome of mammalian cells (e.g., metallothionein promoter) or from mammalian viruses (e.g., the retrovirus long terminal repeat; the adenovirus late promoter; the vaccinia virus 7.5K promoter) can be used. Promoters produced by recombinant DNA or synthetic techniques may also be used to provide for transcription of the nucleic acid sequences. In one embodiment, the promoter is a cytomegalovirus promoter.

Fractionating:

Subjecting a sample to conditions or procedures which separate the components of the sample based on physical or chemical properties such as, but not limited to, size, charge, solubility, or composition. Example of fractionation procedures include, but are not limited to, selective precipitation, organic extraction, size exclusion dialysis or chromatography, such as ion exchange chromatography. In one embodiment, a fraction is a soluble extract or an organic extract of an organism, such as a *Mycobacterium*.

Functionally Equivalent:

Sequence alterations, such as in an epitope of an antigen, that yield the same results as described herein. Such sequence alterations can include, but are not limited to, conservative substitutions, deletions, mutations, frameshifts, and insertions that do not affect the function of the encoded polypeptide.

Heterologous:

Originating from separate genetic sources or species. A polypeptide that is heterologous to an *Mycobacterium* polypeptide originates from a nucleic acid that does not encode the *Mycobacterium* polypeptide. In one specific, non-limiting example, a polypeptide comprising nine consecutive amino acids from an *Mycobacterium* polypeptide, or at most 20 consecutive amino acids from the *Mycobacterium* polypeptide, and a heterologous amino acid sequence includes a β-galactosidase, a maltose binding protein, albumin, hepatitis B surface antigen, or an immunoglobulin amino acid sequence. Generally, an antibody that specifically binds to a protein of interest will not specifically bind to a heterologous protein.

Host Cells:

Cells in which a vector can be propagated and its DNA expressed. The cell may be prokaryotic or eukaryotic. The cell can be mammalian, such as a human cell. The term also includes any progeny of the subject host cell. It is understood that all progeny may not be identical to the parental cell since there may be mutations that occur during replication. However, such progeny are included when the term "host cell" is used.

Hybridization:

To form base pairs between complementary regions of two strands of DNA, RNA, or between DNA and RNA, thereby forming a duplex molecule. Hybridization conditions resulting in particular degrees of stringency will vary depending upon the nature of the hybridization method and the composition and length of the hybridizing nucleic acid sequences. Generally, the temperature of hybridization and the ionic strength (such as the $Na^+$ concentration) of the hybridization buffer will determine the stringency of hybridization. Calculations regarding hybridization conditions for attaining particular degrees of stringency are discussed in Sambrook et al., (1989) *Molecular Cloning*, second edition, Cold Spring Harbor Laboratory, Plainview, N.Y. (chapters 9 and 11).

Inhibiting or Treating a Disease:

Inhibiting a disease, such as tuberculosis, refers to inhibiting the full development of a disease. In several examples, inhibiting a disease refers to lessening symptoms of a tuberculosis. "Treatment" refers to a therapeutic intervention that ameliorates a sign or symptom of a disease or pathological condition related to the disease, such as tuberculosis.

Isolated:

An "isolated" nucleic acid has been substantially separated or purified away from other nucleic acid sequences in the cell of the organism in which the nucleic acid naturally occurs, i.e., other chromosomal and extra chromosomal DNA and RNA. The term "isolated" thus encompasses nucleic acids purified by standard nucleic acid purification methods. The term also embraces nucleic acids prepared by recombinant expression in a host cell as well as chemically synthesized nucleic acids. Similarly, an "isolated" protein has been substantially separated or purified away from other proteins in the cell of the organism in which protein naturally occurs. The term "isolated" thus encompasses proteins purified by standard molecular biology methods. The term also embraces proteins prepared by recombinant expression in a host cell as well as chemically synthesized protein. Examples of isolated nucleic acids or proteins is nucleic acids or proteins that are greater than about 90%, greater than about 95%, greater than about 98%, or greater than about 99% pure.

Label:

A detectable compound or composition that is conjugated directly or indirectly to another molecule to facilitate detection of that molecule. Specific, non-limiting examples of labels include fluorescent tags, enzymatic linkages, and radioactive isotopes.

Linker Sequence:

A linker sequence is an amino acid sequence that covalently links two polypeptide domains. Linker sequences can be included in between a *Mycobacterium* polypeptide, such as TDMH, and a heterologous protein to provide rotational freedom to the linked polypeptide domains and thereby to promote proper domain folding. By way of example, in a recombinant polypeptide comprising two domains, linker sequences can be provided between them, such as a polypeptide comprising *Mycobacterium* polypeptide-linker-heterologous polypeptide. Linker sequences, which are generally between 2 and 25 amino acids in length, are well known in the art and include, but are not limited to, the glycine(4)-serine spacer (GGGGS (SEQ ID NO: 4)×3) described by Chaudhary et al., *Nature* 339:394-397, 1989.

Mammal:

This term includes both human and non-human mammals. Similarly, the term "patient" or "subject" includes both human and veterinary subjects.

*Mycobacteria:*

A genus of aerobic intracellular bacterial organisms. Upon invasion of a host, these organisms survive within endosomal compartments of monocytes and macrophages. Human mycobacterial diseases include tuberculosis (cause by *M. tuberculosis*), Leprosy (caused by *M. leprae*), Bairnsdale ulcers (caused by *M. ulcerans*), and other infections that can be caused by *M. marinum, M. kansasii, M. scrofulaceum, M. szulgai, M. xenopi, M. fortuitum, M. haemophilum, M. chelonei*, and *M. intracelluare. Mycobacterium* strains that were previously considered to be nonpathogenic (such as *M. avium*) are also now known to be major killers of immunosuppressed AIDS patients.

An immune response to *mycobacteria* can involve cell mediated hypersensitivity (DTH) reactions with T cells and macrophages playing major roles in the intracellular killing and walling off (or containing) of the organism (granuloma formation). A T cell response can involve $CD4^+$ lymphocytes that recognize myocbacterial heat shock proteins and immunodominant antigens as well as $CD8^+$ cells.

Nucleic Acid:

A polymer composed of nucleotide units (ribonucleotides, deoxyribonucleotides, related naturally occurring structural variants, and synthetic non-naturally occurring analogs thereof) linked via phosphodiester bonds, related naturally occurring structural variants, and synthetic non-naturally occurring analogs thereof. Thus, the term includes nucleotide polymers in which the nucleotides and the linkages between them include non-naturally occurring synthetic analogs, such as, for example and without limitation, phosphorothioates, phosphoramidates, methyl phosphonates, chiral-methyl phosphonates, 2-O-methyl ribonucleotides, peptide-nucleic acids (PNAs), and the like. Such polynucleotides can be synthesized, for example, using an automated DNA synthesizer. It will be understood that when a nucleotide sequence is represented by a DNA sequence (i.e., A, T, G, C), this also includes an RNA sequence (i.e., A, U, G, C) in which "U" replaces "T."

"Nucleotide" includes, but is not limited to, a monomer that includes a base linked to a sugar, such as a pyrimidine, purine or synthetic analogs thereof, or a base linked to an amino acid, as in a peptide nucleic acid (PNA). A nucleotide is one monomer in a polynucleotide. A nucleotide sequence refers to the sequence of bases in a polynucleotide.

Conventional notation is used herein to describe nucleotide sequences: the left-hand end of a single-stranded nucleotide sequence is the 5'-end; the left-hand direction of a double-stranded nucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand;" sequences on the DNA strand having the same sequence as an mRNA transcribed from that DNA and which are located 5' to the 5'-end of the RNA transcript are referred to as "upstream sequences;" sequences on the DNA strand having the same sequence as the RNA and which are 3' to the 3' end of the coding RNA transcript are referred to as "downstream sequences."

"cDNA" refers to a DNA that is complementary or identical to an mRNA, in either single stranded or double stranded form.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (for example, rRNA, tRNA and mRNA) or a defined sequence of amino acids and the biological properties resulting therefrom. Thus, a gene encodes a protein if transcription and translation of mRNA produced by that gene produces the protein in a cell or other biological system. Both the coding strand, the nucleotide sequence of which is identical to the mRNA sequence and is usually provided in sequence listings, and non-coding strand, used as the template for transcription, of a gene or cDNA can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns. In some examples, a nucleic acid encodes a disclosed antigen.

Oligonucleotide:

A linear polynucleotide sequence of between 5 and 100 nucleotide bases in length.

Operably Linked:

A first nucleic acid sequence is operably linked with a second nucleic acid sequence when the first nucleic acid sequence is placed in a functional relationship with the second nucleic acid sequence. For instance, a promoter is operably linked to a coding sequence if the promoter effects the transcription or expression of the coding sequence. Generally, operably linked DNA sequences are contiguous and, where necessary to join two protein coding regions, the open reading frames are aligned.

ORF (Open Reading Frame):

A series of nucleotide triplets (codons) coding for amino acids without any termination codons. These sequences are usually translatable into a polypeptide.

Peptide Modifications:

*Mycobacterium* polypeptides, such as TDMH, include synthetic embodiments of peptides described herein. In addition, analogues (non-peptide organic molecules), derivatives (chemically functionalized peptide molecules obtained starting with the disclosed peptide sequences) and variants (homologs) of these proteins can be utilized in the methods described herein. Each polypeptide of the invention is comprised of a sequence of amino acids, which may be either L- and/or D-amino acids, naturally occurring and otherwise.

Peptides may be modified by a variety of chemical techniques to produce derivatives having essentially the same activity as the unmodified peptides, and optionally having other desirable properties. For example, carboxylic acid groups of the protein, whether carboxyl-terminal or side chain, may be provided in the form of a salt of a pharmaceutically-acceptable cation or esterified to form a $C_1$-$C_{16}$ ester, or converted to an amide of formula $NR_1R_2$ wherein $R_1$ and $R_2$ are each independently H or $C_1$-$C_{16}$ alkyl, or combined to form a heterocyclic ring, such as a 5- or 6-membered ring. Amino groups of the peptide, whether amino-terminal or side chain, may be in the form of a pharmaceutically-acceptable acid addition salt, such as the HCl, HBr, acetic, benzoic, toluene sulfonic, maleic, tartaric and other organic salts, or may be modified to $C_1$-$C_{16}$ alkyl or dialkyl amino or further converted to an amide.

Hydroxyl groups of the peptide side chains may be converted to $C_1$-$C_{16}$ alkoxy or to a $C_1$-$C_{16}$ ester using well-recognized techniques. Phenyl and phenolic rings of the peptide side chains may be substituted with one or more halogen atoms, such as fluorine, chlorine, bromine or iodine, or with $C_1$-$C_{16}$ alkyl, $C_1$-$C_{16}$ alkoxy, carboxylic acids and esters thereof, or amides of such carboxylic acids. Methylene groups of the peptide side chains can be extended to homologous $C_2$-$C_4$ alkylenes. Thiols can be protected with any one of a number of well-recognized protecting groups, such as acetamide groups. Those skilled in the art will also recognize methods for introducing cyclic structures into the peptides of this invention to select and provide conformational constraints to the structure that result in enhanced stability.

Peptidomimetic and organomimetic embodiments are envisioned, whereby the three-dimensional arrangement of the chemical constituents of such peptido- and organomimetics mimic the three-dimensional arrangement of the peptide backbone and component amino acid side chains, resulting in such peptido- and organomimetics of a *Mycobacterium* polypeptide having measurable or enhanced ability to generate an immune response. For computer modeling applications, a pharmacophore is an idealized, three-dimensional definition of the structural requirements for biological activity. Peptido- and organomimetics can be designed to fit each pharmacophore with current computer modeling software (using computer assisted drug design or CADD). See Walters, "Computer-Assisted Modeling of Drugs", in Klegerman & Groves, eds., 1993, *Pharmaceutical Biotechnology*, Interpharm Press: Buffalo Grove, Ill., pp. 165-174 and *Principles of Pharmacology* Munson (ed.) 1995, Ch. 102, for descriptions of techniques used in CADD. Also included are mimetics prepared using such techniques.

Pharmaceutical Agent or Drug:

A chemical compound or composition capable of inducing a desired therapeutic or prophylactic effect when properly administered to a subject.

Pharmaceutically Acceptable Carriers:

The pharmaceutically acceptable carriers useful with the polypeptides and nucleic acids described herein are conventional. *Remington's Pharmaceutical Sciences*, by E. W. Martin, Mack Publishing Co., Easton, Pa., 15th Edition (1975), describes compositions and formulations suitable for pharmaceutical delivery of the fusion proteins herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Polynucleotide:

A linear nucleotide sequence, including sequences of greater than 100 nucleotide bases in length.

Polypeptide:

Any chain of amino acids, regardless of length or post-translational modification (e.g., glycosylation or phosphorylation). A "peptide" is a chain of amino acids that is less than 100 amino acids in length. In one embodiment, a "peptide" is a portion of a polypeptide, such as at about 10, 20, 30, 40, 50, or 100 contiguous amino acids of a polypeptide that is greater than 100 amino acids in length.

Portion of a Nucleic Acid Sequence:

At least 10, 20, 30 or 40 contiguous nucleotides of the relevant sequence, such as a sequence encoding an antigen. In some instances it would be advantageous to use a portion consisting of 50 or more nucleotides. For instance, when describing a portion of an antigen (such as an antigenic epitope), it may be advantageous to remove a portion of the relevant sequence comprising at least 10, 20, 30, 40 or 50 nucleotides up to a length.

Probes and Primers:

Nucleic acid probes and primers may readily be prepared based on the nucleic acids provided by this invention. A probe comprises an isolated nucleic acid attached to a detectable label or reporter molecule. Typical labels include radioactive isotopes, ligands, chemiluminescent agents, and enzymes. Methods for labeling and guidance in the choice of labels appropriate for various purposes are discussed, e.g., in Sambrook et al. (1989) and Ausubel et al. (1987).

Primers are short nucleic acids, preferably DNA oligonucleotides 15 nucleotides or more in length. Primers may be annealed to a complementary target DNA strand by nucleic acid hybridization to form a hybrid between the primer and the target DNA strand, and then extended along the target DNA strand by a DNA polymerase enzyme. Primer pairs can be used for amplification of a nucleic acid sequence, e.g., by the polymerase chain reaction (PCR) or other nucleic-acid amplification methods known in the art.

Methods for preparing and using probes and primers are described, for example, in *Molecular Cloning: A Laboratory Manual,* 2nd ed., vol. 1-3, ed. Sambrook et al., Cold Spring Harbor Laboratory Press, Cold Spring Harbor, N.Y., 1989, and *Current Protocols in Molecular Biology*, ed. Ausubel et al., Greene Publishing and Wiley-Interscience, New York, 1987 (with periodic updates). PCR primer pairs can be derived from a known sequence, for example, by using computer programs intended for that purpose such as Primer (Version 0.5, © 1991, Whitehead Institute for Biomedical Research, Cambridge, Mass.).

Primer Pairs:

Two primers (one "forward" and one "reverse") that can be used for amplification of a nucleic acid sequence, for example by polymerase chain reaction (PCR) or other in vitro nucleic-acid amplification methods. The forward and reverse primers of a primer pair do not hybridize to overlapping complementary sequences on the target nucleic acid sequence.

Preventing or Treating a Disease:

"Preventing" a disease refers to inhibiting the full development of a disease, for example in a person who is known to be at risk of infection with a *Mycobacterium*, such as *M. tuberculosis*. An example of a person with a known predisposition is someone living with a person diagnosed with tuberculosis, health care professionals, or someone otherwise known to have been exposed to *M. tuberculosis*. "Treatment" refers to a therapeutic intervention that ameliorates a sign or symptom of a disease or pathological condition, such as tuberculosis, after it has begun to develop.

Promoter:

A promoter is an array of nucleic acid control sequences which direct transcription of a nucleic acid. A promoter includes necessary nucleic acid sequences near the start site of transcription, such as, in the case of a polymerase II type promoter, a TATA element. A promoter also optionally includes distal enhancer or repressor elements which can be located as much as several thousand base pairs from the start site of transcription. The promoter can be a constitutive or an inducible promoter. A specific, non-limiting example of a promoter is the HCMV IE promoter.

Purified:

The term purified does not require absolute purity; rather, it is intended as a relative term. Thus, for example, a purified protein preparation is one in which the protein is more pure than the protein in its originating environment within a cell. A preparation of an protein is typically purified such that the protein represents at least 50% of the total protein content of the preparation. However, more highly purified preparations may be required for certain applications. For example, for such applications, preparations in which the protein, such as TDMH, comprises at least 75% or at least 90%, 91%, 92%, 93%, 94%, 95%, 96%, 97%, 98%, or 99% of the total protein content may be employed.

Recombinant:

A recombinant nucleic acid or polypeptide is one that has a sequence that is not naturally occurring or has a sequence that is made by an artificial combination of two or more otherwise separated segments of sequence. This artificial combination is often accomplished by chemical synthesis or, more commonly, by the artificial manipulation of isolated segments of nucleic acids, e.g., by genetic engineering techniques.

Sequence Identity:

The similarity between amino acid sequences is expressed in terms of the similarity between the sequences, otherwise referred to as sequence identity. Sequence identity is frequently measured in terms of percentage identity (or similarity or homology); the higher the percentage, the more similar the two sequences are. Variants of antigen polypeptides will possess a relatively high degree of sequence identity when aligned using standard methods.

Methods of alignment of sequences for comparison are well known in the art. Altschul et al. (1994) presents a detailed consideration of sequence alignment methods and homology calculations. The NCBI Basic Local Alignment Search Tool (BLAST) (Altschul et al., 1990) is available from several sources, including the National Center for Biotechnology Information (NCBI, Bethesda, Md.) and on the Internet, for use in connection with the sequence analysis programs blastp, blastn, blastx, tblastn and tblastx. It can be accessed at the NCBI website. A description of how to determine sequence identity using this program is available at the NCBI website, as are the default parameters.

Variants of antigenic polypeptides, such as a *Mycobacterium* polypeptide, such as TDMH, are typically characterized by possession of at least 50% sequence identity counted over the full length alignment with the amino acid sequence of a native antigen sequence using the NCBI Blast 2.0, gapped blastp set to default parameters. Proteins with even greater similarity to the reference sequences will show increasing percentage identities when assessed by this method, such as at least 60%, at least 65%, at least 70%, at least 75%, at least 80%, at least 90% or at least 95% sequence identity. When less than the entire sequence is being compared for sequence identity, variants will typically possess at least 75% sequence identity over short windows of 10-20 amino acids, and may possess sequence identities of at least 85% or at least 90% or 95% depending on their similarity to the reference sequence. Methods for determining sequence identity over such short windows are described at the NCBI website. Variants of polypeptides also retain the biological activity of the native polypeptide.

Sensitivity and Specificity:

Statistical measurements of the performance of a binary classification test. Sensitivity measures the proportion of actual positives which are correctly identified (e.g., the percentage of samples that are identified as including nucleic acid from a *Mycobacterium*). Specificity measures the proportion of negatives which are correctly identified (e.g., the percentage of samples that are identified as not including nucleic acid from a particular *Mycobacterium*).

Target Nucleic Acid Molecule:

A nucleic acid molecule whose detection, quantitation, qualitative detection, or a combination thereof, is intended. The nucleic acid molecule need not be in a purified form. Various other nucleic acid molecules can also be present with the target nucleic acid molecule. For example, the target nucleic acid molecule can be a specific nucleic acid molecule (which can include RNA or DNA), the amplification of which is intended. In some examples, a target nucleic acid includes a region of a *Mycobacterium* genome.

Therapeutically Active Polypeptide:

An agent, such as a hydrolase, that can reduce or prevent biofilm formation, or that reduces a sign or symptom of an infection with a *Mycobacterium*. Therapeutically active molecules can also be made from nucleic acids. Examples of a nucleic acid based therapeutically active molecule is a nucleic acid sequence that encodes a hydrolase, wherein the nucleic acid sequence is operably linked to a control element such as a promoter.

Therapeutically Effective Dose:

A dose sufficient to prevent advancement, or to cause regression of the disease, or which is capable of relieving symptoms caused by the disease. The dose can also be sufficient to cause hydrolysis of a *Mycobacterium*, and reduce or prevent biofilm formation. In one embodiment, a therapeutically effective dose is a dose sufficient to prevent advancement or relieve symptoms of tuberculosis.

Transduced and Transformed:

A virus or vector "transduces" a cell when it transfers nucleic acid into the cell. A cell is "transformed" by a nucleic acid transduced into the cell when the DNA becomes stably replicated by the cell, either by incorporation of the nucleic acid into the cellular genome, or by episomal replication. As used herein, the term transformation encompasses all techniques by which a nucleic acid molecule might be introduced into such a cell, including transfection with viral vectors, transformation with plasmid vectors, and introduction of naked DNA by electroporation, lipofection, and particle gun acceleration.

Tuberculosis (TB):

A disease that is generally caused by *Mycobacterium tuberculosis* that usually infects the lungs. However, other "atypical" *mycobacteria* such as *M. kansasii* may produce a similar clinical and pathologic appearance of disease.

Transmission of *M. tuberculosis* (Mtb) occurs by the airborne route in confined areas with poor ventilation. In more than 90% of cases, following infection with *M. tuberculosis*, the immune system prevents development of disease from *M. tuberculosis*, often called, active tuberculosis. However, not all of the *M. tuberculosis* is killed, and thus tiny, hard capsules are formed. "Primary tuberculosis" is seen disease that develops following an initial infection, usually in children. The initial focus of infection is a small subpleural granuloma accompanied by granulomatous hilar lymph node infection. Together, these make up the Ghon complex. In nearly all cases, these granulomas resolve and there is no further spread of the infection. "Secondary tuberculosis" is seen mostly in adults as a reactivation of previous infection (or reinfection), particularly when health status declines. The granulomatous inflammation is much more florid and widespread. Typically, the upper lung lobes are most affected, and cavitation can occur. Dissemination of tuberculosis outside of lungs can lead to the appearance of a number of uncommon findings with characteristic patterns that include skeletal tuberculosis, genital tract tuberculosis, urinary tract tuberculosis, central nervous system (CNS) tuberculosis, gastrointestinal tuberculosis, adrenal tuberculosis, scrofula, and cardiac tuberculosis. "Latent" tuberculosis is an Mtb infection in an individual that can be detected by a diagnostic assay, such as, but not limited to a tuberculin skin test (TST) wherein the infection does not produce symptoms in that individual. "Active" tuberculosis is a symptomatic Mtb infection in a subject.

Microscopically, the inflammation produced with TB infection is granulomatous, with epithelioid macrophages and Langhans giant cells along with lymphocytes, plasma cells, maybe a few polymorphonuclear cells, fibroblasts with collagen, and characteristic caseous necrosis in the center. The inflammatory response is mediated by a type IV hypersensitivity reaction, and skin testing is based on this reaction. In some examples, tuberculosis can be diagnosed by a skin test, an acid fast stain, an auramine stain, or a combination thereof. The most common specimen screened is sputum, but the histologic stains can also be performed on tissues or other body fluids.

Tuberculosis is a frequent complication of HIV infection. Tubercuolosis infection in subjects infected with a human immunodeficiency virus (HIV) can spread readily and progress rapidly to active disease. Specific symptoms of lung disease due to Mtb infection include chronic cough and spitting blood. Other symptoms of TB disease include fatigue, loss of appetite, weight loss, fever and drenching night sweats.

Vector:

A nucleic acid molecule as introduced into a host cell, thereby producing a transduced or transformed host cell. A vector may include nucleic acid sequences that permit it to replicate in a host cell, such as an origin of replication. A vector may also include one or more selectable marker gene and other genetic elements known in the art. Vectors include plasmid vectors, including plasmids for expression in gram negative and gram positive bacterial cells. Exemplary vectors include those for expression in *E. coli* and *Salmonella*. Vectors also include viral vectors, such as, but are not limited to, retrovirus, orthopox, avipox, fowlpox, capripox, suipox, adenoviral, herpes virus, alpha virus, baculovirus, Sindbis virus, vaccinia virus and poliovirus vectors. Vectors also include vectors for expression in yeast cells Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." All publications, patent applications, patents, and other references mentioned herein are incorporated by reference in their entirety. In case of conflict, the present specification, including explanations of terms, will control. In addition, the materials, methods, and examples are illustrative only and not intended to be limiting.

TDMH and Methods of Use

Methods are provided herein for treating a *Mycobacterium* infection, and for treating a biofilm. Methods are also provided for detection. These methods are of use to treat and/or detect *Mycobacterium*, such as, but not limited to, *M. tuberculosis, M. avium, M. marinum, M. bovis* (BCG), and *M. smegmatis*. The methods include the use of trehalose dimycolate hydrolase (TDMH), also known as Msmeg_1529. In one embodiment, TDMH has the amino acid sequence set forth as:

(SEQ ID NO: 1)
VISLRKPARLAAFASAVLCAGAALATGPAPVASAEPCSDIEVVFARGTSE

PAGIGRVGQALTDAIRNQVGGRTVSTYGVNYPATYDFLAAADGANDATNR

IATLAEQCPSTRVVLGGYSQGAAVVDMLLGIPPLGNKVGNFGSAPPLPSN

-continued
LMNNVAAVAVFGNPSAKFGIPVTSRFGGRAIDACSDGDPICSDGRNPFAH

THYESSPFIPQAAGLIAGLV*.

In another embodiment, TDMH has the amino acid sequence set forth as:

(SEQ ID NO: 2)
MTMAIVISLRKPARLAAFASAVLCAGAALATGPAPVASAEPCSDIEVVFA

RGTSEPAGIGRVGQALTDAIRNQVGGRTVSTYGVNYPATYDFLAAADGAN

DATNRIATLAEQCPSTRVVLGGYSQGAAVVDMLLGIPPLGNKVGNFGSAP

PLPSNLMNNVAAVAVFGNPSAKFGIPVTSRFGGRAIDACSDGDPICSDGR

NPFAHTHYESSPFIPQAAGLIAGLV

In a further embodiment, TDMH is encoded by the nucleic acid sequence set forth as:

(SEQ ID NO: 3)
GTGATTTCCCTCCGGAAGCCGGCCCGGTTGGCCGCGTTCGCCTCAGCAGT

CCTGTGCGCCGGTGCCGCGCTGGCCACAGGCCCCGCCCCGGTCGCCTCCG

CAGAGCCCTGCTCCGACATCGAGGTGGTGTTCGCGCGCGGCACGAGTGAA

CCCGCCGGTATCGGCCGCGTCGGCCAGGCGCTGACCGATGCGATCCGCAA

TCAGGTCGGTGGCCGCACGGTCAGCACCTACGGCGTGAACTACCCCGCCA

CGTACGACTTCCTGGCCGCGGCCGACGGCGCCAACGACGCCACCAACCGC

ATCGCGACGCTGGCCGAGCAGTGCCCGTCGACGCGCGTCGTGCTGGGCGG

CTACTCGCAGGGCGCGGCCGTGGTCGACATGCTGCTGGGGATCCCGCCCC

TGGGCAACAAGGTGGGCAACTTCGGTTCCGCCCCGCCGCTGCCGAGCAAC

CTCATGAACAACGTCGCGGCCGTCGCGGTGTTCGGCAACCCGTCGGCCAA

GTTCGGCATCCCGGTCACCAGCCGGTTCGGCGGCCGCGCGATCGACGCGT

GCAGCGACGGCGACCCGATCTGTTCGGACGGTCGGAACCCGTTCGCGCAC

ACGCATTACGAGAGCTCGCCGTTCATCCCGCAGGCAGCAGGGCTGATCGC

GGGTCTGGTTTAG

The TDMH of use in the methods disclosed herein is at least 70% identical to the amino acid sequence set forth as SEQ ID NO: 1 and/or SEQ ID NO: 2. In other embodiments of the method, the polypeptide is at least 75%, at least 80%, at least 85%, at least 90%, at least 95%, at least 96%, at least 97%, at least 98%, or at least 99% identical to the amino acid sequence set forth as SEQ ID NO: 1 and/or SEQ ID NO: 2. In one embodiment, the polypeptide comprises the amino acid sequence set forth as SEQ ID NO: 1. In another embodiment, the polypeptide comprises the amino acid sequence set forth as SEQ ID NO: 2. In a further embodiment the polypeptide is encoded by the nucleic acid sequence set forth as SEQ ID NO: 2. In other embodiments, the nucleic acid sequence is at least 70%, at least 80%, at least 85%, at least 90%, at least 95%, at least 96%, at least 97%, at least 98%, or at least 99% identical to the nucleic acid sequence set forth as SEQ ID NO: 2. Generally, the TDMH polypeptide hydrolyses trehalose, 6,6'-dimycolate (TDM).

In some embodiments, the polypeptide includes at most 1, at most 2, at most 3, at most 4 or at most 5 conservative substitutions in the amino acid sequence set forth as SEQ ID NO: 1 or SEQ ID NO: 2, wherein the polypeptide hydrolyses trehalose, 6,6'-dimycolate (TDM). In additional embodiments, the TDMH is TDMH S124A. In additional embodiments, the polypeptide includes, or consists of, the amino acid sequence set forth as SEQ ID NO: 1 or SEQ ID NO: 2.

The TDMH polypeptides disclosed herein can be chemically synthesized by standard methods, or can be produced recombinantly. An exemplary process for polypeptide production is described in Lu et al., *Federation of European Biochemical Societies Letters.* 429:31-35, 1998. The TDMH or variant thereof can also be isolated by methods including preparative chromatography and immunological separations.

If desired, polypeptides can also be chemically synthesized by emerging technologies. One such process is described in W. Lu et al., *Federation of European Biochemical Societies Letters.* 429:31-35, 1998. Polypeptides can also be produced using molecular genetic techniques, such as by inserting a nucleic acid encoding TDMH into an expression vector, introducing the expression vector into a host cell, and isolating the polypeptide (see below).

Polynucleotides encoding TDMH or a variant thereof include DNA, cDNA and RNA sequences which encode the polypeptide of interest. Silent mutations in the coding sequence result from the degeneracy (i.e., redundancy) of the genetic code, whereby more than one codon can encode the same amino acid residue. Thus, for example, leucine can be encoded by CTT, CTC, CTA, CTG, TTA, or TTG; serine can be encoded by TCT, TCC, TCA, TCG, AGT, or AGC; asparagine can be encoded by AAT or AAC; aspartic acid can be encoded by GAT or GAC; cysteine can be encoded by TGT or TGC; alanine can be encoded by GCT, GCC, GCA, or GCG; glutamine can be encoded by CAA or CAG; tyrosine can be encoded by TAT or TAC; and isoleucine can be encoded by ATT, ATC, or ATA. Tables showing the standard genetic code can be found in various sources (e.g., L. Stryer, 1988, Biochemistry, 3.sup.rd Edition, W.H. 5 Freeman and Co., NY).

A nucleic acid encoding a TDMH polypeptide can be cloned or amplified by in vitro methods, such as the polymerase chain reaction (PCR), the ligase chain reaction (LCR), the transcription-based amplification system (TAS), the self-sustained sequence replication system (3SR) and the Qβ replicase amplification system (QB). For example, a polynucleotide encoding the protein can be isolated by polymerase chain reaction of cDNA using primers based on the DNA sequence of the molecule. A wide variety of cloning and in vitro amplification methodologies are well known to persons skilled in the art. PCR methods are described in, for example, U.S. Pat. No. 4,683,195; Mullis et al., *Cold Spring Harbor Symp. Quant. Biol.* 51:263, 1987; and Erlich, ed., *PCR Technology*, (Stockton Press, NY, 1989). Polynucleotides also can be isolated by screening genomic or cDNA libraries with probes selected from the sequences of the desired polynucleotide under stringent hybridization conditions.

The polynucleotides encoding a TDMH polypeptide include a recombinant DNA which is incorporated into a vector, into an autonomously replicating plasmid or virus, or into the genomic DNA of a prokaryote or eukaryote, or which exists as a separate molecule (such as a cDNA) independent of other sequences. The nucleotides of the invention can be ribonucleotides, deoxyribonucleotides, or modified forms of either nucleotide. The term includes single and double forms of DNA.

In one embodiment, vectors are used for expression in yeast such as *S. cerevisiae* or *Kluyveromyces lactis*. Several promoters are known to be of use in yeast expression systems such as the constitutive promoters plasma membrane $H^+$-ATPase (PMA1), glyceraldehyde-3-phosphate dehydrogenase (GPD), phosphoglycerate kinase-1 (PGK1), alcohol dehydrogenase-1 (ADH1), and pleiotropic drug-resistant pump (PDR5). In addition, may inducible promoters are of use, such as GAL1-10 (induced by galactose), PHO5 (induced by low extracellular inorganic phosphate), and tandem heat shock HSE elements (induced by temperature elevation to 37° C.). Promoters that direct variable expression in response to a titratable inducer include the methionine-responsive MET3 and MET25 promoters and copper-dependent CUP1 promoters. Any of these promoters may be cloned into multicopy (2µ) or single copy (CEN) plasmids to give an additional level of control in expression level. The plasmids can include nutritional markers (such as URA3, ADE3, HIS1, and others) for selection in yeast and antibiotic resistance (AMP) for propagation in bacteria. Plasmids for expression on *K. lactis* are known, such as pKLAC1. Thus, in one example, after amplification in bacteria, plasmids can be introduced into the corresponding yeast auxotrophs by methods similar to bacterial transformation.

The TDMH polypeptides and variants can be expressed in a variety of yeast strains. For example, seven pleiotropic drug-resistant transporters, YOR1, SNQ2, PDR5, YCF1, PDR10, PDR11, and PDR15, together with their activating transcription factors, PDR1 and PDR3, have been simultaneously deleted in yeast host cells, rendering the resultant strain sensitive to drugs. Yeast strains with altered lipid composition of the plasma membrane, such as the erg6 mutant defective in ergosterol biosynthesis, can also be utilized. Proteins that are highly sensitive to proteolysis can be expressed in a yeast lacking the master vacuolar endopeptidase Pep4, which controls the activation of other vacuolar hydrolases. Heterologous expression in strains carrying temperature-sensitive (ts) alleles of genes can be employed if the corresponding null mutant is invisable.

Viral vectors can also be prepared encoding the TDMH polypeptides and variants disclosed herein. A number of viral vectors have been constructed, including polyoma, SV40 (Madzak et al., 1992, J. Gen. Virol., 73:15331536), adenovirus (Berkner, 1992, Cur. Top. Microbiol. Immunol., 158:39-6; Berliner et al., 1988, Bio Techniques, 6:616-629; Gorziglia et al., 1992, J. Virol., 66:4407-4412; Quantin et al., 1992, Proc. Nad. Acad. Sci. USA, 89:2581-2584; Rosenfeld et al., 1992, Cell, 68:143-155; Wilkinson et al., 1992, Nucl. Acids Res., 20:2233-2239; Stratford-Perricaudet et al., 1990, Hum. Gene Ther., 1:241-256), vaccinia virus (Mackett et al., 1992, Biotechnology, 24:495-499), adeno-associated virus (Muzyczka, 1992, Curr. Top. Microbiol. Immunol., 158:91-123; On et al., 1990, Gene, 89:279-282), herpes viruses including HSV and EBV (Margolskee, 1992, Curr. Top. Microbiol. Immunol., 158:67-90; Johnson et al., 1992, J. Virol., 66:29522965; Fink et al., 1992, Hum. Gene Ther. 3:11-19; Breakfield et al., 1987, Mol. Neurobiol., 1:337-371; Fresse et al., 1990, Biochem. Pharmacol., 40:2189-2199), Sindbis viruses (H. Herweijer et al., 1995, Human Gene Therapy 6:1161-1167; U.S. Pat. No. 5,091,309 and U.S. Pat. No. 5,217,879), alphaviruses (S. Schlesinger, 1993, Trends Biotechnol. 11:18-22; I. Frolov et al., 1996, Proc. Natl. Acad. Sci. USA 93:11371-11377) and retroviruses of avian (Brandyopadhyay et al., 1984, Mol. Cell. Biol., 4:749-754; Petropouplos et al., 1992, J. Virol., 66:3391-3397), murine (Miller, 1992, Curr. Top. Microbiol. Immunol., 158:1-24; Miller et al., 1985, Mol. Cell. Biol., 5:431-437; Sorge et al., 1984, Mol. Cell. Biol., 4:1730-1737; Mann et al., 1985, J. Virol., 54:401-407), and human origin (Page et al., 1990, J. Virol., 64:5370-5276; Buchschalcher et al., 1992, J. Virol., 66:2731-2739). Baculovirus (*Autographa californica* multinuclear polyhedrosis virus; AcMNPV) vectors are also known in the art, and may be obtained from commercial sources (such as PharMingen, San Diego, Calif.; Protein Sciences Corp., Meriden, Conn.; Stratagene, La Jolla, Calif.).

Thus, in one embodiment, the polynucleotide encoding a TDMH polypeptide is included in a viral vector. Suitable vectors include retrovirus vectors, *orthopox* vectors, avipox vectors, fowlpox vectors, capripox vectors, suipox vectors, adenoviral vectors, herpes virus vectors, alpha virus vectors, baculovirus vectors, Sindbis virus vectors, vaccinia virus vectors and poliovirus vectors. Specific exemplary vectors are poxvirus vectors such as vaccinia virus, fowlpox virus and a highly attenuated vaccinia virus (MVA), adenovirus, baculovirus and the like.

Methods of Treatment

Methods are disclosed herein for treating a subject with a *Mycobacterium* infection. The methods include administering to a subject a therapeutically effective amount of a TDMH polypeptide, or a variant thereof, or a polynucleotide encoding the polypeptide. These methods are of use to treat an infection with a *Mycobacterium*, such as, but not limited to, *M. tuberculosis, M. avium, M. marinum, M. bovis* (BCG), and *M. smegmatis*. The TDMH polypeptide hydrolyses trehalose, 6,6'-dimycolate (TDM).

Amounts effective for these uses will depend upon the severity of the disease, the general state of the patient's health, and the robustness of the patient's immune system. In one example, a therapeutically effective amount of the compound is that which provides either subjective relief of a symptom(s) or an objectively identifiable improvement as noted by the clinician or other qualified observer. In additional examples, a therapeutically effective amount is an amount sufficient to prevent development of symptom in a subject infected with a *Mycobacterium*, such as, but not limited to, *M. tuberculosis, M. avium, M. marinum, M. bovis* (BCG), and *M. smegmatis*.

Pharmaceutical compositions that include the disclosed TDMH polypeptides, variants, and or polynucleotides, alone or in combination with additional antimicrobial agents (for example antibacterial agents, antifungal agents, or antiprotozoal agents, or combinations thereof) can be formulated with an appropriate pharmaceutically acceptable carrier, depending upon the particular mode of administration chosen. In one embodiment, a polypeptide or polynucleotide can be formulated with an appropriate pharmaceutically acceptable carrier, depending upon the particular mode of administration chosen. In some embodiments, a TDMH polypeptide, a variant thereof, or a nucleic acid encoding the TDMH polypeptide or variant, is formulated in combination with an additional antimicrobial agent (for example, at least one, at least two, at least three, or more additional antimicrobial agents) can be formulated with an appropriate pharmaceutically acceptable carrier, depending upon the particular mode of administration chosen. The antimicrobial agent can be any antimicrobial agent of interest, including, but not limited to, erythromycin, clarithromycin or azithromycin. In some examples, the pharmaceutical composition consists essentially of the TDMH polypeptide, or a variant thereof, or a nucleic acid encoding the TDMH polypeptide or variant, and a pharmaceutically acceptable carrier. In the present disclosure, "consists essentially of" indicates that additional active compounds (for example additional antimicrobial agents) are not included in the composition, but that other inert agents (such as fillers, wetting agents, or the like) can be included, and "consists of" indicates that additional agents are not included in the composition.

The pharmaceutically acceptable carriers and excipients useful in this disclosure are conventional. See, e.g., *Remington: The Science and Practice of Pharmacy*, The University of the Sciences in Philadelphia, Editor, Lippincott, Williams, & Wilkins, Philadelphia, Pa., 21$^{st}$ Edition (2005). For instance, parenteral formulations usually comprise injectable fluids that are pharmaceutically and physiologically acceptable fluid vehicles such as water, physiological saline, other balanced salt solutions, aqueous dextrose, glycerol or the like. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, pH buffering agents, or the like, for example sodium acetate or sorbitan monolaurate. Excipients that can be included are, for instance, other proteins, such as human serum albumin or plasma preparations.

In some embodiments, the TDMH polypeptide or a variant thereof, or polynucleotide encoding the polypeptide, is included in a controlled release formulation, for example, a microencapsulated formulation. Various types of biodegradable and biocompatible polymers, methods can be used, and methods of encapsulating a variety of synthetic compounds, proteins and nucleic acids, have been well described in the art (see, for example, U.S. Pat. Publication Nos. 2007/0148074; 2007/0092575; and 2006/0246139; U.S. Pat. Nos. 4,522,811; 5,753,234; and 7,081,489; PCT Publication No. WO/2006/052285; Benita, *Microencapsulation: Methods and Industrial Applications*, 2$^{nd}$ ed., CRC Press, 2006).

In other examples, the TDMH polypeptide, a variant thereof, or a nucleic acid encoding the TDMH polypeptide or variant, is included in a nanodispersion system. Nanodispersion systems and methods for producing such nanodispersions are well known to one of skill in the art. See, e.g., U.S. Pat. No. 6,780,324; U.S. Pat. Publication No. 2009/0175953. For example, a nanodispersion system includes a biologically active agent and a dispersing agent (such as a polymer, copolymer, or low molecular weight surfactant). Exemplary polymers or copolymers include polyvinylpyrrolidone (PVP), poly(D,L-lactic acid) (PLA), poly(D,L-lactic-co-glycolic acid (PLGA), poly(ethylene glycol). Exemplary low molecular weight surfactants include sodium dodecyl sulfate, hexadecyl pyridinium chloride, polysorbates, sorbitans, poly(oxyethylene)alkyl ethers, poly(oxyethylene)alkyl esters, and combinations thereof. In some examples, the nanodispersion is prepared using the solvent evaporation method. See, e.g., Kanaze et al., *Drug Dev. Indus. Pharm.* 36:292-301, 2010; Kanaze et al., *J. Appl. Polymer Sci.* 102:460-471, 2006.

The dosage form of the pharmaceutical composition will be determined by the mode of administration chosen. For instance, in addition to injectable fluids, topical, inhalation, oral and suppository formulations can be employed. Topical preparations can include eye drops, ointments, sprays, patches and the like. Inhalation preparations can be liquid (e.g., solutions or suspensions) and include mists, sprays and the like. Oral formulations can be liquid (e.g., syrups, solutions or suspensions), or solid (e.g., powders, pills, tablets, or capsules). Suppository preparations can also be solid, gel, or in a suspension form. For solid compositions, conventional non-toxic solid carriers can include pharmaceutical grades of mannitol, lactose, cellulose, starch, or magnesium stearate. Actual methods of preparing such dosage forms are known, or will be apparent, to those skilled in the art.

The pharmaceutical compositions can be formulated in unit dosage form, suitable for individual administration of precise dosages. In specific, non-limiting examples, a unit dosage contains from about 1 microgram to about 1 g of a TDMH polypeptide or variant thereof (such as about 50 micrograms to about 900 mg, about 100 micrograms to about 750 mg, about 500 micrograms to about 400 mg, about 10 mg to about 250 mg, about 100 mg to about 900 mg, about 250 mg to about 750 mg, or about 400 mg to about 600 mg. In other specific, non-limiting examples, a unit dosage contains from about 1 microgram per kilogram to about 500 milligrams per kilogram, about 100 micrograms per kilogram to about 5 milligrams per kilogram, or about 1 microgram per kilogram to about 50 micrograms per kilogram. The amount of active compound(s) administered will be dependent on the subject being treated, the severity of the affliction, and the manner of administration, and is best left to the judgment of the prescribing clinician. Within these bounds, the formulation to be administered will contain a quantity of the active component(s) in amounts effective to achieve the desired effect in the subject being treated.

The agents disclosed herein can be administered to a subject in need of treatment using any suitable means known in the art. Methods of administration include, but are not limited to, intraductal, intradermal, intramuscular, intraperitoneal, parenteral, intravenous, subcutaneous, vaginal, rectal, intranasal, inhalation, oral or by gene gun. Intranasal administration refers to delivery of the compositions into the nose and nasal passages through one or both of the nares and can comprise delivery by a spraying mechanism or droplet mechanism, or through aerosolization of the nucleic acid or virus. Administration of the compositions by inhalant can be through the nose or mouth via delivery by spraying or droplet mechanisms. Delivery can be directly to any area of the respiratory system via intubation. Parenteral administration is generally achieved by injection. Injectables can be prepared in conventional forms, either as liquid solutions or suspensions, solid forms suitable for solution of suspension in liquid prior to injection, or as emulsions. Injection solutions and suspensions can be prepared from sterile powders, granules, and tablets. Administration can be systemic or local.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, anti-oxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

Administration can be accomplished by single or multiple doses. The dose required will vary from subject to subject depending on the species, age, weight and general condition of the subject, the particular therapeutic agent being used and its mode of administration. An appropriate dose can be determined by one of ordinary skill in the art using only routine experimentation.

In some examples, the agents are administered using an enteral or parenteral administration route. Suitable enteral administration routes include, for example, oral, rectal, or intranasal delivery. Suitable parenteral administration routes include, for example, intravascular administration (such as intravenous bolus injection, intravenous infusion, intra-arterial bolus injection, intra-arterial infusion and catheter instillation into the vasculature); subcutaneous injection or deposition, including subcutaneous infusion (such as by osmotic pumps); direct application to the tissue of interest, for example by a catheter or other placement device (e.g., a suppository or an implant comprising a porous, non-porous, or gelatinous material); and inhalation. Particularly suitable administration routes are injection, infusion and direct injection into a target tissue.

In some embodiments, liposomes are used to deliver an agent to a subject. Liposomes can also increase the blood half-life of the gene products or nucleic acids. Suitable liposomes for use in the invention can be formed from standard vesicle-forming lipids, which generally include neutral or negatively charged phospholipids and a sterol, such as cholesterol. The selection of lipids is generally guided by consideration of several factors, such as the desired liposome size and half-life of the liposomes in the blood stream. A variety of methods are known in the art for preparing liposomes (see, for example, Szoka et al., *Ann. Rev. Biophys. Bioeng.* 9:467, 1980; and U.S. Pat. Nos. 4,235,871; 4,501,728; 4,837,028; and 5,019,369).

Appropriate doses of small molecule agents depend upon a number of factors known to those or ordinary skill in the art, e.g., a physician. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide of the invention. Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram).

Methods of Treating a Biofilm

Bacterial biofilm formation can lead to localized infections as well as difficult to treat, and sometimes fatal, systemic infections, such as bacteremia (the presence of bacteria in the blood) and bacterial sepsis (multiple organ failure caused by the spread of bacteria or their products through the bloodstream). The extracellular substances that comprise the biofilm matrix can act as a barrier that protects and isolates the bacteria resident within the biofilm from normal immunological defense mechanisms, such as antibodies and phagocytes, as well as from antimicrobial agents including surfactants, antibacterial enzymes and antibiotics. The biofilm also facilitates the growth and proliferation of bacteria resident within the biofilm. Therefore there is an urgent need for novel antimicrobials (for example, antibacterials) that are effective against *Mycobacterium*.

It has been surprisingly demonstrated that the disclosed TDMH polypeptide exhibits antibacterial activity against a wide range of species of *Mycobacterium* and is effective at killing these bacteria in biofilms. Thus, the disclosed TDMH polypeptide, or variants thereof that hydrolyses trehalose, 6,6'-dimycolate (TDM), can be used to inhibit the growth (or multiplication) of, inhibit further growth (or multiplication) of, or control the growth (or multiplication) of a number of species of *Mycobacterium* or surface attached bacteria (for example, surface attached bacteria of a biofilm). These species include, but are not limited to, *M. tuberculosis, M. avium, M. marinum, M. bovis* (BCG), and *M. smegmatis*.

Disclosed herein is a method for treating a *Mycobacterium* biofilm. In a one embodiment, a surface infected with a biofilm is selected for treatment. In one embodiment, the method involves contacting a biofilm with an effective amount of the disclosed TDMH polypeptide, or variants thereof that has an anti-bacterial activity against the biofilm, thereby treating the biofilm. In one embodiment of the method, contacting a biofilm involves contacting a mass, aggregation, or community of *Mycobacterium* attached to a surface and the associated extracellular substances produced by one or more of the attached bacteria. In another embodiment, the method involves contacting *Mycobacterium*, such as a culture, with an effective amount of TDMH polypeptide, or variants thereof, wherein the TDMH polypeptide or variant thereof, has an anti-bacterial activity against *Mycobacterium*. In some embodiments, about 50 to about 500 µg, such as about 100 to about 400 µg, such as about 200 to about 300 µg, such as about 240 to about 280 µg, such as about 250 to about 260 µg TDMH polypeptide, or a variant thereof, is utilized.

In one embodiment, the method includes contacting a biofilm of *Mycobacteria* with a TDMH polypeptide, or variant thereof. As disclosed herein, the TDMH polypeptide, or a variant thereof, has an anti-bacterial activity against a biofilm of *Mycobacterium*, such as, but not limited to, *M. tuberculosis, M. avium, M. marinum, M. bovis* (BCG), and *M. smegmatis*. In one embodiment, an antimicrobial activity is an increase in cell lysis. Thus, in one embodiment of the method, contacting the biofilm or planktonic cells with the TDMH polypeptide or a variant thereof, increases bacterial cell lysis in the biofilm, or increases lysis of *Mycobacterium* compared to a biofilm in the absence of the TDMH polypeptide. In particular embodiments, an increase in bacterial cell lysis is at least a 2%, at least a 5%, at least a 10%, at least a 20%, at least a 30%, at least a 40%, at least a 50%, at least a 75%, at least a 100%, at least a 150%, at least a 200% or more increase in lysed cells in the biofilm. In another embodiment, an antibacterial activity is a reduction in biofilm cell viability. In particular embodiments, a reduction in cell viability is a reduction of viable cells by at least 25%, at least 50%, at least 75%, at least 80%, at least 90%, at least 95%, at least 96%, at least 97%, at least 98%, at least 99%, or 100%. In one specific non-limiting example, the antibacterial activity of the TDMH polypeptide, or a variant thereof, can be measured by the production or the size of a clear zone on a microbial lawn surrounding a bacterial colony, or by measuring the clarity of a culture.

In some embodiments of the method, the biofilm is attached to a living or non-living surface. In other particular embodiments, a non-living surface in the subject is a surface of a medical device, such as the surface of an indwelling medical device. Examples of indwelling medical devices include intravascular catheters (for example, intravenous and intra-arterial), right heart flow-directed catheters, Hickman catheters, arteriovenous fistulae, catheters used in hemodialysis and peritoneal dialysis (for example, silastic, central venous, Tenckhoff, and Teflon catheters), vascular access ports, indwelling urinary catheters, urinary catheters, silicone catheters, ventricular catheters, synthetic vascular prostheses (for example, aortofemoral and femoropopliteal), prosthetic heart valves, prosthetic joints (for example, prosthetic knee or hip joints), orthopedic implants, penile implants, shunts (for example, Scribner, Torkildsen, central nervous system, portasystemic, ventricular, ventriculoperitoneal), intrauterine devices, dental prostheses (for example, permanent dentures or partial implants), stents (for example, ureteral stents), artificial voice prostheses, tympanostomy tubes, gastric feeding tubes, endotracheal tubes, pacemakers, implantable defibrillators, tubing, cannulas, probes, blood monitoring devices, needles, mouth guards, night guards, dentures, orthodontic retainers, contact lenses, and the like. However, the medical device need not be implantable, nor need it have direct therapeutic activity. The device can be, for example, a storage device, such as a medical storage device, for example a contact lens case.

In particular embodiments, the indwelling medical devices includes surgically implantable devices (for example, a pacemaker, prosthetic heart valves, shunts, prosthetic joints, orthopedic implants, dental implants or synthetic vascular prostheses). In other particular embodiments, the indwelling medical device is not surgically implanted, but is routinely inserted and removed by the subject (for example, a mouth guard, a night guard, removable dentures, an orthodontic retainer, or a contact lens). In some embodiments, the medical device has a lumen (for example, a catheter). In other embodiments, the non-living surface to be treated is a surface of an object that is not an indwelling medical device (a surface that is external to the subject). In particular embodiments, the non-living surface is on or near a food preparation area (for example, a counter, a table, or a floor), on food preparation utensils (for example, a knife), on a household surface (for example, a shower or a toilet), or a fluid-conducting or gas-conducting object having a lumen (such as a water, oil, gas, or sewage pipe, or tubing).

In one embodiment of the method, the medical device is suitable for surgical implantation within the body of the subject. In another embodiment of the method, the medical device is surgically implanted within the body of the subject. In a further embodiment, the medical device is non-permanently inserted in the subject. In yet a further embodiment, the medical device is not introduced, inserted, or surgically implanted in the subject.

In some embodiments, the disclosed TDMH polypeptide, or a variant thereof, is administered to the non-living surface before a biofilm is formed in order to inhibit the formation of a biofilm on the surface. Alternatively, at the first indication of biofilm formation, the methods may be used to inhibit further biofilm formation (or growth or multiplication). Suitable coatings for indwelling medical devices include various hydrogel coatings. The disclosed TDMH polypeptide, or a variant thereof, can be incorporated into the hydrogel before or after the hydrogel is applied to the medical device. In some embodiments, the hydrogel coating of the medical device includes an additional antimicrobial agent, such as an antibiotic, a bacteriocin, an antimicrobial peptide, or a bacteriophage. In particular embodiments of the method, the TDMH polypeptide, or a variant thereof, does not have the same amino acid sequence as the $E.\ coli$ K-12 colicin E2 polypeptide. The biofilm also can be treated with an additional antimicrobial agent of interest, including, but not limited to, erythromycin, clarithromycin or azithromycin.

The living or non-living surfaces can have surfaces composed of thermoplastic or polymeric materials such as polyethylene, Dacron, nylon, polyesters, polytetrafluoroethylene, polyurethane, latex, silicone elastomers, and the like. The surfaces may be smooth or rough, for example, a smooth polymeric surface of a catheter lumen or a relatively rough Dacron patch for repairing an abdominal or vascular defect. Metallic surfaces are also amenable to treatment with the disclosed compositions.

Various methods can be employed to treat the living or non-living surfaces with the disclosed TDMH polypeptide, or a variant thereof. The disclosed TDMH polypeptide, or a variant thereof, may be applied to (for example, a composition comprising the TDMH polypeptide, or a variant thereof, may be painted, sprayed, or soaked on) the living or non-living surface. In particular embodiments, the living or non-living surface is dipped or immersed in a composition comprising the TDMH polypeptide, or a variant thereof. One specific, non-limiting example of the method is to flush the lumen of a medical device with a composition containing the disclosed TDMH polypeptide, or a variant thereof. In particular embodiments of the methods, the flushing solution is composed of sterile media or sterile normal saline solutions in addition to the disclosed TDMH polypeptide, or a variant thereof. In some embodiments of the method, the medical device is removed from the subject prior to treatment. In other embodiments of the method, the subject is administered the disclosed TDMH polypeptide, or a variant thereof. Without being bound by theory, the disclosed methods improve the operability or reduce the infectious potential of a medical device, or reduce the occlusion of a pipe or tubing, caused by the growth or encrustation of the biofilm on the surface.

In further embodiments, an additional agent used is to facilitate removing the biofilm deposited on a surface. For example, the compositions can include a surfactant or an antibacterial enzyme, or combinations thereof. Exemplary surfactants include, but are not limited to, biosurfactants (such as glycolipids, lipopeptides, depsipeptides, phospholipids, substituted fatty acids, lipopolysaccharides, surlactin, surfactin, visconsin, and rhamnolipids), sodium dodecyl sulfate, quaternary ammonium compounds, alkyl pyridinium iodides, Tween 80, Tween, 85, Triton X-100, hexadecyl pyridinium chloride, polysorbates, sorbitans, poly(oxyethylene) alkyl ethers, poly(oxyethylene)alkyl esters, and the like. Exemplary antibacterial enzymes are, but not limited to, a lytic enzyme, an acylase, an aminopeptidase, an amylase, a carbohydrase, a carboxypeptidase, a catalase, a cellulase, a chitinase, a cutinase, a cyclodextrin glycosyltransferase, a deoxyribonuclease, an esterase, an alpha-galactosidase, a beta-galactosidase, a glucoamylase, an alpha-glucosidase, a beta-glucosidase, a haloperoxidase, an invertase, a laccase, a lipase, a mannosidase, an oxidase, a pectinolytic enzyme, a peptidoglutaminase, a peroxidase, a phytase, a polyphenoloxidase, a proteolytic enzyme, a ribonuclease, a transglutaminase, a xylanase, and lysostaphin.

Methods of Diagnosis

Diagnosis of tuberculosis is commonly achieved using a skin test, which involves intradermal exposure to tuberculin PPD (protein-purified derivative). Antigen-specific T cell responses result in measurable induration at the injection site by 48 to 72 hours after injection, which indicates exposure to Mycobacterial antigens. However, the sensitivity and specificity of this test are not ideal; individuals vaccinated with BCG cannot be distinguished from infected individuals. Accordingly, there is a need in the art for improved diagnostic methods for detecting *Mycobacterium*, including *M. tuberculosis*.

Methods are provided herein for detecting *Mycobacterium* in a sample. These methods include contacting a sample from a subject suspected of having a *Mycobacterium* infection with an effective amount of trehalose dimycolase hydrolase (TDMH), or a variant thereof that hydrolyses trehalose, 6,6'-dimycolate (TDM), and performing reaction to identify the *Mycobacterium*, such as to detect a *Mycobacterium* polypeptide or polynucleotide. The sample can be from a subjected suspected of having an infection with *M. tuberculosis, M. avium, M. marinum, M. bovis* (BCG), or *M. smegmatis*.

In some embodiments, the sample is obtained from a subject suspected of having an *M. tuberculosis* infection, and the assay is used to diagnose the *M. tuberculosis* infection in the subject. In some embodiments, the subject has a paucibacilliary infection. In other embodiments, the subject has a subclinical infection. In further embodiments, the subject is co-infected with a human immunodeficiency virus (HIV). The 2008 data indicate that 1.4 million of the TB cases were in people living with HIV/AIDS who are particularly likely to be paucibacillary (see World Health Organization (2009) Global Tuberculosis Control: Epidemiology, Strategy, Financing. WHO Report. WHO/HTM/TB/2009.411, available on the internet). Thus, specific non-limiting examples, the use of trehalose dimycolase hydrolase (TDMH), or a variant thereof, allows detection of as little as 5, 10, 15 or 20 bacilli in a sample, such as *M. tuberculosis*.

Diagnostic reagents include the use of polynucleotide sequences encoding a *Mycobacterium* polypeptide. *Mycobacterium* infection can be detected by detecting the presence, absence, or level of mRNA encoding a *Mycobacterium* polypeptide in a biological sample. In several examples, hybridization assays are utilized, such as Northern blot or dot blot assays. The methods can include the use of methods that amplify and/or detect *Mycobacterium* nucleic acids. Thus, the methods can include, but are not limited to, the use of an amplification reaction such as polymerase chain reaction (PCR), including reverse transcriptase PCR (RT-PCR). Thus, in additional examples, PCR based assays are utilized.

In some embodiments a sample from the subject is contacted with a trehalose dimycolate hydrolase or a variant thereof that hydrolyses trehalose, 6,6'-dimycolate (TDM), as disclosed above. The sample can be any sample of interest, including, but not limited to, a sputum sample, a blood sample, serum sample, plasma sample, biopsy sample, bronchiolar lavage sample. In some embodiments the sample is diluted in a buffer, such as, but not limited to phosphate buffered saline or Tris buffered saline. In some embodiments, the sample is a sputum sample. The sputum sample can be clarified. Exemplary protocols for clarifying sputum are provided in the examples section and additional protocols are known in the art.

The sample, or diluted sample, can be incubated with the treahalose dimocyolate hydrolase for a sufficient amount of time to hydrolyze trehalose, 6,6'-dimycolate. In some embodiments the sample, or diluted sample is incubated at about 35 to 39° C., such as about 36 to 37° C., such as about 37° C. In other embodiments, the sample or diluted sample is incubated for about 30 minutes to about 120 minutes, such as about 45 minutes to 90 minutes, such as for about 30 minutes, 35 minutes, 40 minutes, 45 minutes, 50 minutes, 55 minutes 60 minutes, 65 minutes, 70 minutes, 75 minute, 80 minutes, 85 minutes, or 90 minutes. In some embodiments, about 50 to about 500 µg, such as about 100 to about 400 µg, such as about 200 to about 300 µg, such as about 240 to about 280 µg, such as about 250 to about 260 µg TDMH polypeptide, or a variant thereof, is utilized.

The trehalose dimycolate hydrolase can be any trehalose dimycolate hydrolase or variant thereof that hydrolyses trehalose, 6,6'-dimycolate (TDM). Thus, in some examples, the sample is contacted with an effective amount of a polypeptide including the amino acid sequence set forth as SEQ ID NO: 1 or SEQ ID NO: 2, or an effective amount of a polypeptide at least 70% identical to the amino acid sequence set forth as SEQ ID NO: 1 or SEQ ID NO: 2, such as 80%, 90%, 91%, 92%, 93%, 94%, 95%, 96%, 97%, 98% or 99% identical, wherein the polypeptide has trehalose dimycolate hydrolase activity. In other embodiments, the polypeptide includes an amino acid sequence set forth as SEQ ID NO: 1 or SEQ ID NO: 2 with at most 1, 2, 3, 4, or 5 amino acid substitutions that hydrolyses trehalose, 6,6'-dimycolate (TDM).

General methods for mRNA extraction are well known in the art and are disclosed in standard textbooks of molecular biology, including Ausubel et al., Current Protocols of Molecular Biology, John Wiley and Sons (1997). Methods for RNA extraction from paraffin embedded tissues are disclosed, for example, in Rupp and Locker, Lab Invest. 56:A67 (1987), and De Andres et al., BioTechniques 18:42044 (1995). In particular, RNA isolation can be performed using purification kit, buffer set and protease from commercial manufacturers, such as QIAGEN®, according to the manufacturer's instructions. For example, total RNA from cells in culture (such as those obtained from a subject) can be isolated using QIAGEN® RNeasy mini-columns. Other commercially available RNA isolation kits include MASTERPURE®. Complete DNA and RNA Purification Kit (EPICENTRE® Madison, Wis.), and Paraffin Block RNA Isolation Kit (Ambion, Inc.). Total RNA from tissue samples can be isolated using RNA Stat-60 (Tel-Test). RNA prepared a biological sample can be isolated, for example, by cesium chloride density gradient centrifugation.

Methods for quantitating mRNA are well known in the art. In one example, the method utilizes reverse transcriptase polymerase chain reaction (RT-PCR). Generally, the first step in gene expression profiling by RT-PCR is the reverse transcription of the RNA template into cDNA, followed by its exponential amplification in a PCR reaction. The two most commonly used reverse transcriptases are avian myeloblastosis virus reverse transcriptase (AMV-RT) and Moloney murine leukemia virus reverse transcriptase (MMLV-RT). The reverse transcription step is typically primed using specific primers, random hexamers, or oligo-dT primers, depending on the circumstances and the goal of expression profiling. For example, extracted RNA can be reverse-transcribed using a GeneAmp RNA PCR kit (Perkin Elmer, Calif., USA), following the manufacturer's instructions. The derived cDNA can then be used as a template in the subsequent PCR reaction.

Although the PCR step can use a variety of thermostable DNA-dependent DNA polymerases, it typically employs the Taq DNA polymerase, which has a 5'-3' nuclease activity but lacks a 3'-5' proofreading endonuclease activity. Thus, Taq-Man® PCR typically utilizes the 5'-nuclease activity of Taq or Tth polymerase to hydrolyze a hybridization probe bound to its target amplicon, but any enzyme with equivalent 5' nuclease activity can be used. Two oligonucleotide primers are used to generate an amplicon typical of a PCR reaction. A third oligonucleotide, or probe, is designed to detect nucleotide sequence located between the two PCR primers. The probe is non-extendible by Taq DNA polymerase enzyme, and is labeled with a reporter fluorescent dye and a quencher fluorescent dye. Any laser-induced emission from the reporter dye is quenched by the quenching dye when the two dyes are located close together as they are on the probe. During the amplification reaction, the Taq DNA polymerase enzyme cleaves the probe in a template-dependent manner. The resultant probe fragments disassociate in solution, and signal from the released reporter dye is free from the quenching effect of the second fluorophore. One molecule of reporter dye is liberated for each new molecule synthesized, and detection of the unquenched reporter dye provides the basis for quantitative interpretation of the data.

TAQMAN® RT-PCR can be performed using commercially available equipment, such as, for example, ABI PRISM 7700® sequence detection system (Perkin-Elmer-Applied Biosystems, Foster City, Calif., USA), or Lightcycler (Roche Molecular Biochemicals, Mannheim, Germany). In one embodiment, the 5' nuclease procedure is run on a real-time quantitative PCR device such as the ABI PRISM 7700® sequence detection system. The system includes of thermocycler, laser, charge-coupled device (CCD), camera and computer. The system amplifies samples in a 96-well format on a thermocycler. During amplification, laser-induced fluorescent signal is collected in real-time through fiber optics cables for all 96 wells, and detected at the CCD. The system includes software for running the instrument and for analyzing the data.

However, any type of thermal cycler apparatus can be used for the amplification of JCV virus nucleic acids as described above and/or the determination of hybridization. Examples of suitable apparatuses include PTC-100® Peltier Thermal Cycler (MJ Research, Inc.; San Francisco, Calif.), a ROBOCYCLER® 40 Temperature Cycler (Agilent/Stratagene; Santa Clara, Calif.), or GeneAmp® PCR System 9700 (Applied Biosystems; Foster City, Calif.). For real-time PCR, any type of real-time thermocycler apparatus can be used. For example, ICYCLER IQ™ or CFX96™ real-time detection systems (Bio-Rad, Hercules, Calif.), LIGHTCYCLER® systems (Roche, Mannheim, Germany), ABI™ systems such as the 7000, 7300, 7500, 7700, or 7900 systems (Applied Biosystems; Foster City, Calif.), or an MX4000™, MX3000™ or MX3005™ qPCR system (Agilent/Stratagene; Santa Clara, Calif.), DNA ENGINE OPTICON® Continuous Fluorescence Detection System (Bio-Rad, Hercules, Calif.), ROTOR-GENE® Q real-time cycler (Qiagen, Valencia, Calif.), or SMARTCYCLER® system (Cepheid, Sunnyvale, Calif.) can be used to amplify and detect nucleic acid sequences in real-time. In some embodiments, real-time PCR is performed using a TAQMAN® array format, for example, a microfluidic card in which each well is pre-loaded with primers and probes for a particular target. The reaction is initiated by adding a sample including nucleic acids and assay reagents (such as a PCR master mix) and running the reactions in a real-time thermocycler apparatus.

In some examples, 5'-Nuclease assay data are initially expressed as Ct, or the threshold cycle. As discussed above, fluorescence values are recorded during every cycle and represent the amount of product amplified to that point in the amplification reaction. The point when the fluorescent signal is first recorded as statistically significant is the threshold cycle (Ct).

To minimize errors and the effect of sample-to-sample variation, RT-PCR is can be performed using an internal standard. The ideal internal standard is expressed at a constant level among different tissues, and is unaffected by the experimental treatment. RNAs most frequently used to normalize patterns of gene expression are mRNAs for the housekeeping genes glyceraldehyde-3-phosphate-dehydrogenase (GAPDH), beta-actin, and 18S ribosomal RNA.

A more recent variation of the RT-PCR technique is the real time quantitative PCR, which measures PCR product accumulation through a dual-labeled fluorigenic probe (i.e., TAQMAN® probe). Real time PCR is compatible both with quantitative competitive PCR, where internal competitor for each target sequence is used for normalization, and with quantitative comparative PCR using a normalization gene contained within the sample, or a housekeeping gene for RT-PCR (see Held et al., Genome Research 6:986 994, 1996). Quantitative PCR is also described in U.S. Pat. No. 5,538,848, the disclosure of which is incorporated herein by reference. Related probes and quantitative amplification procedures are described in U.S. Pat. No. 5,716,784 and U.S. Pat. No. 5,723,591, the disclosures of which are incorporated herein by reference. Instruments for carrying out quantitative PCR in microtiter plates are available from PE Applied Biosystems, 850 Lincoln Centre Drive, Foster City, Calif. 94404 under the trademark ABI PRISM® 7700.

The steps of a representative protocol for quantitating gene expression using fixed, paraffin-embedded tissues as the RNA source, including mRNA isolation, purification, primer extension and amplification are given in various published journal articles (see Godfrey et al. J. Molec. Diagnostics 2: 84 91, 2000; K. Specht et al., Am. J. Pathol. 158: 419 29, 2001). Briefly, a representative process starts with cutting about 10 µm thick sections of paraffin-embedded tissue sample. The RNA is then extracted, and protein and DNA are removed. After analysis of the RNA concentration, RNA repair and/or amplification steps can be included, if necessary, and RNA is reverse transcribed using gene specific promoters followed by RT-PCR.

An alternative quantitative nucleic acid amplification procedure is described in U.S. Pat. No. 5,219,727, which is incorporated herein by reference. In this procedure, the amount of a target sequence in a sample is determined by simultaneously amplifying the target sequence and an internal standard nucleic acid segment. The amount of amplified DNA from each segment is determined and compared to a standard curve to determine the amount of the target nucleic acid segment that was present in the sample prior to amplification.

In some embodiments of this method, the expression of a "housekeeping" gene or "internal control" can also be evaluated. These terms are meant to include any constitutively or globally expressed gene whose presence enables an assessment of cytokine mRNA levels. Such an assessment comprises a determination of the overall constitutive level of gene transcription and a control for variations in RNA recovery.

In some embodiments, a subject receiving therapy can be monitored for the presence of the *Mycobacterium*. A decrease in the amount of the *Mycobacterium* nucleic acids in a sample from the subject, as compared to a control, indicates that the therapy is effective.

The disclosure is illustrated by the following non-limiting Examples.

EXAMPLES

Trehalose 6,6'-dimycolate (TDM) is a major non-covalently associated glycolipid of the mycobacterial cell envelope. While TDM is a virulence factor in *Mycobacterium*

*tuberculosis*, its conserved abundance in other mycobacterial species, including the non-pathogenic *mycobacteria*, suggests a broader structural role of the glycolipid in architectural organization of the envelope. Exposure to an esterase from *Mycobacterium smegmatis* (Msmeg_1529), hydrolyzing the ester linkage of TDM, triggers lysis of *M. tuberculosis, Mycobacterium bovis* BCG, and *Mycobacterium marinum*. Lysis is highly rapid and efficient, approximately 99% viability loss within 2-hour exposure, in both growing and stationary phase bacteria. TDM is the primary target of TDM hydrolase during lysis, which could be competitively inhibited by an excess of purified TDM, as well as abolished by a catalytic mutation in the esterase. TDM therefore is a surface-exposed and indispensible structural component of *mycobacteria* that can be targeted for rapid clearance as well as sensitive diagnosis of mycobacterial infections. Enzyme-mediated lysis can be used as a therapeutic agent for XDR and MDR-TB, as well as to detection of *mycobacteria* in a clinical sample.

Example 1

Materials and Methods

Strains and Media:

Liquid cultures of *M. tuberculosis* (except mc$^2$7000), *M. bovis* (BCG) and *M. avium* were grown at 37° C. either in 7H9OADC or Sauton's media with 0.05% Tween-80. For plate culture 7H11OADC or Sauton's media agar was used. mc$^2$7000 was grown similarly, except its media contained 100 μg/mL of pantothenic acid. For *M. smegmatis*, OADC was replaced with ADC in 7H9 broth or plate culture. *M. marinum* was grown at room temperature in 7H9OADCTw liquid medium or 7H11 agar. *E. coli* (DH5α) was grown at 37° C. in Luria broth or LB agar.

In Vitro Lytic Activity of TDMH:

Cells at OD of 0.5 (log-phase) or OD of 3.0 (stationary phase) were harvested, washed and resuspended in either PBST or other culture media as required. Specified amounts of TDMH were mixed with specified number of bacilli and incubated at 37° C. At regular time intervals, an aliquot was diluted and plated for enumeration. An equal volume of storage buffer was used as a negative control for each experiment. Where necessary, 100 μg of either purified TDM (purchased from Sigma), purified apolar and polar lipids (Ojha et al., J Biol Chem 285: 17380-17389, 2010), or purified preparations of mAGP and PIM$_2$ (Ojha et al., supra, 2010) were dried in the reaction tube and suspended in 100 μL PBST by sonication at 55° C. for 10 minutes. To the lipid suspension, cells (10$^7$ cfu/mL) and TDMH (0.8 μM) were added and incubated for two days at 37° C. prior to enumerating the viable bacilli. For the plate assay, 500 μL of 10$^6$ cfu/mL log-phase cells was spread on a Sauton's agar plate and 200 μg of purified TDMH was spotted in the center. An equal volume of storage buffer was spotted as a negative control on a separate plate with bacilli.

ATP Release Assay:

*M. tuberculosis* (mc$^2$ 7000) was grown to OD of 0.5. Cells were harvested, washed with PBS and diluted to 10$^8$/ml in PBST. 8 μM of TDMH was added to 1 mL cell suspension and rotated at 37° C., At regular time intervals 100 μl samples was removed and ATP content was determined by adding 100 μl of ENLITEN® rLuciferase/Luciferin reagent (Promega), and the luminescence was measured using a Monolight 2010 luminometer.

Lipid Analysis:

mc$^2$7000 cultures (OD of 0.5) were labeled with $^{14}$C-acetate for six hours, washed, resuspended in 250 μL of PBST at a density of 10$^9$ cfu/mL, mixed with either 8 μM TDMH or an equal volume of storage buffer at 37° C. At specific time intervals apolar and polar lipids were extracted in petroleum ether as published (Ohja et al, J Biol Chem 285: 17380-17389, 2010). The extracted lipids equivalent to 5000 cpm from each sample were spotted on a one-dimensional TLC, and developed in either 97:3 chloroform:methanol for FM analysis, 90:10:1 chloroform:methanol: water for TDM analysis, or 80:20:2 chloroform:methanol:ammonium hydroxide for TMM analysis, or 65:25:4 chloroform:methanol:water for PIM$_2$ analysis as described earlier (Belisle et al., Science 276: 1420-1422, 1997: Ohja et al., supra, 2010; Besra GS Preperations of cell wall fractions from *mycobacteria*. In: Parish T, Stoker NG, editors. *Mycobacteria* Protocols. Totowa, N.J.: Humana Press. pp. 91-10, 1998). Purified $^{14}$C-FM, $^{14}$C-TDM, $^{14}$C-TMM, $^{14}$C-Palmitic acid and $^{14}$C-PIM$_2$ were used as references as required. For 2D-TLC, amounts equivalent to 35000 counts of each sample were analyzed as described previously (Ojha et al., supra, 2010).

Catalytic Activity of TDMH on TDM, TMM and PIM$_2$:

$^{14}$C-TDM or $^{14}$C-TMM, equivalent to 100,000 cpm was homogeneously suspended in the assay buffer as described earlier (Ojha et al., supra, 2010). The homogenate was then mixed with either 5 μg of TDMH (wt), 5 μg of TDMH (S124A) or an equal volume of storage buffer, and incubated at 37° C. for two hours. The lipids in the reaction mixture were then sequentially extracted with an equal volume of petroleum ether followed by dichloromethane for TDM and TMM, or chloroform:methanol (2:1) for PIM$_2$. The organic layer was dried, and analyzed on TLC developed in 97:3 chloroform:methanol for TDM and TMM (Ojha et al., supra, 2010), or 65:25:4 chloroform:methanol:water for PIM$_2$ (Schue et al., FASEB J 24: 1893-1903, 2010).

Nucleic Acids Detection and Real-Time PCR:

For determining nucleic acids, 10 μL of 10$^7$ cfu/mL of *M. tuberculosis* (Erdman) was mixed with either 1 μL (13 μg) of TDMH, or 1 μL of storage buffer in PBST with 3 mM L-Asparagine (PBSTA), and incubated at 37° C. At various time intervals reactions were inactivated by heat (80° C. for 20 minutes) and 1 μL of the reaction was place in a Nanophotometer to measure the NA contents. For RT-PCR, in a 10 μL reaction either 10$^4$, 10$^3$, or, 10$^2$ bacilli of *M. tuberculosis* (Erdman) were mixed with either 1 μL (13 μg) of TDMH or 1 μL of storage buffer in PBSTA and incubated for 30 minutes at 37° C., then heat-inactivated at 80° C. for 20 minutes. 1 μL of the treated mixture was directly added as a template to the molecular beacon based RT-PCR described previously (El-Hajj et al., J Clin Microbiol 39: 4131-4137, 2001), with 500 nM each of the *M. tuberculosis* 16S rRNA-specific forward and reverse primers, 200 nM of molecular beacon and 5 μL of 2×RT-PCR master mix (Applied Biosystems). The amplification condition was: 95° C.—10 minutes, followed by 40 cycles of; 95° C.—30 seconds, 58° C.—60 seconds and 72° C.-30 seconds in Applied Biosystems instrument (StepOnePlus RT-PCR System). The forward and reverse primer sequences were 5'-GAGATACTCGAGTGGCGAAC-3' (SEQ ID NO: 5) and 5'-GGCCGGCTACCCGTCGTC-3' (SEQ ID NO: 6) respectively, and the molecular beacon was: 5'-fluorescein-GCGCCCGCGGCCTATCAGCTTGTTG-GTGGCGC-dabcyl-3' (SEQ ID NO: 7).

Electron Microscopy: Sample Preparation and Analysis:

mc$^2$7000 cells (10$^9$ cfu/mL) mixed with TDMH (8 μM) in PBST, harvested after a 12-hour incubation, put on ice, and transferred to Leica EMPACT 2 (Leica Microsystems) membrane carriers (1.5 mm×0.2 mm) for high-pressure freezing (HPF) in EMPACT 2 (Leica), at an average of 2000 bar (Studer et al., The Journal of Cell Biology 17: 208-212, 2001). The frozen cells were then transferred to a freeze-substitution machine Leica EM AFS (Leica) for a 5-day solvent substitution. Briefly, frozen samples were warmed up from 196° C. to −90° C. over three days in a precooled (−90° C.) 1% $OsO_4$ and 0.1% Uranyl Acetate mixture dissolved in acetone. Samples were then gradually warmed up to room temperature over 18 hours and subsequently rinsed in acetone for further resin infiltration and embedding. Ultrathin sections (65 nm) were cut with a Reichart Ultracut and laid on 300 mesh carbon coated EM grids. The thin sections were post-stained with 2% uranyl acetate in methanol for 10 minutes, followed by Reynold's lead citrate (Reynolds et al., The Journal of Cell Biology 17: 208-212, 1993) for 7 minutes, and were examined with a Tecnai F20 electron microscope (FEI) loaded with a Gatan 4 k×4 k camera (Gatan).

Example 2

Effect of Msmeg_1529 on *Mycobacteria*

Trehalose 6,6'-dimycolate (TDM) is a major non-covalently associated glycolipid of the mycobacterial cell envelope. While TDM is a virulence factor in *Mycobacterium tuberculosis*, its conserved abundance in other mycobacterial species, including the non-pathogenic *mycobacteria*, suggests a broader structural role of the glycolipid in architectural organization of the envelope. Exposure to an esterase from *Mycobacterium smegmatis* (Msmeg_1529) (Hoffman et al., Proc Natl Acad Sci USA 105, 3963, 2008; Ojha et al., J Biol Chem 285, 17380, 2010), hydrolyzing the ester linkage of TDM, triggers lysis of *M. tuberculosis, Mycobacterium bovis* BCG, and *Mycobacterium marinum*. Lysis is highly rapid and efficient, approximately 99% viability loss within 2-hour exposure, in both growing and stationary phase bacteria. TDM is the primary target of TDM hydrolase during lysis, which could be competitively inhibited by an excess of purified TDM, as well as abolished by a catalytic mutation in the esterase. TDM therefore is a surface-exposed and indispensible structural component of *mycobacteria* that can be targeted for rapid clearance as well as sensitive diagnosis of mycobacterial infection.

Figure 9:
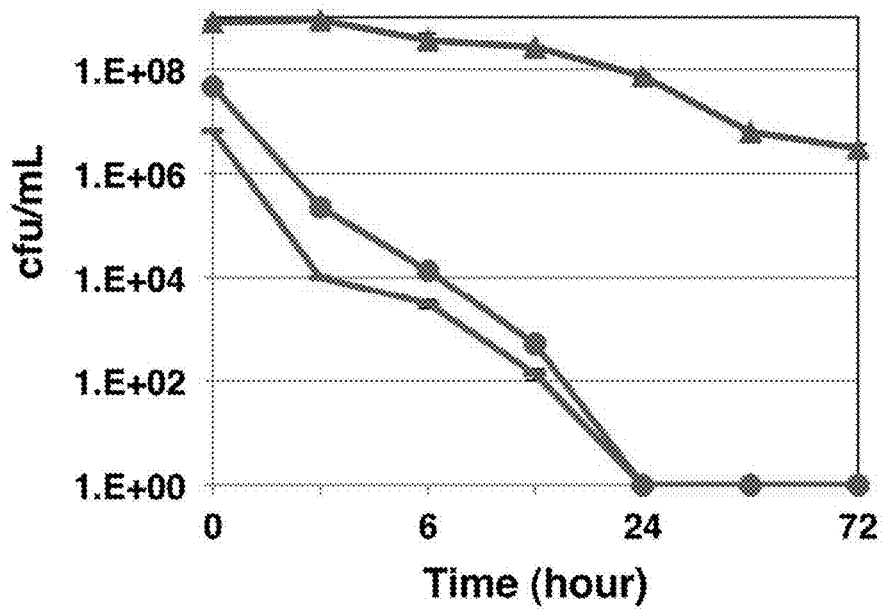
FIG. 9. Exposure of various densities of *M. tuberculosis* (mc27000) to SmM of TDMH over 72-hour period.

Approximately $10^6$ cfu/mL of *M. tuberculosis* (H37Rv) bacilli were incubated with increasing concentrations of the purified recombinant TDMH for 24 hours in PBS with Tween-80 (PBST). FIG. 1A shows that the viability of the population was reduced by 100-fold or more after exposure to 0.8 µM or higher concentrations of the enzyme. At a 10-fold excess concentration (8 µM), the enzyme could reduce the viability of $10^8$ cfu/mL of bacilli in less than two hours, but higher density ($10^9$ cfu/mL) required longer exposure (FIG. 9).

Figure 1B:
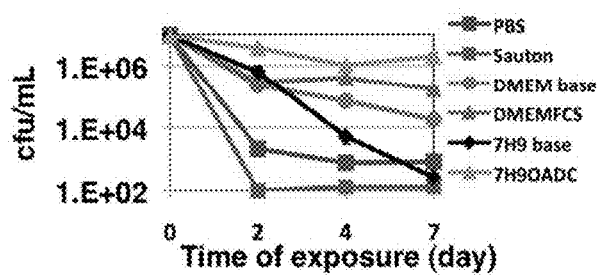
Figure 1C:
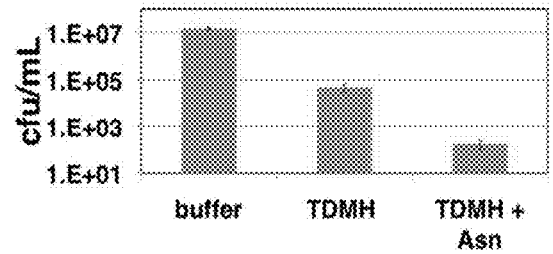
Figure 1D:
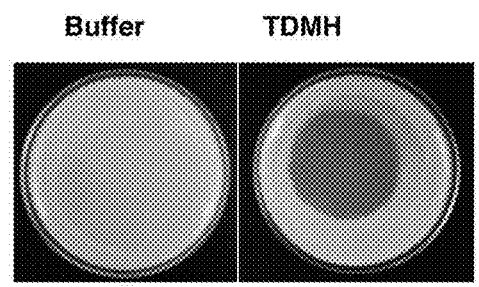
Figure 10A:
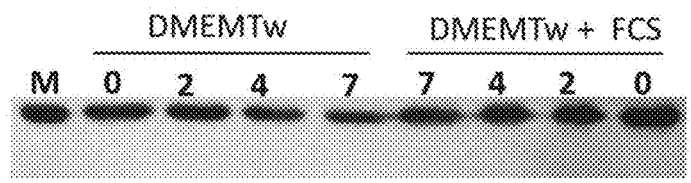
FIGS. 10A-10C. Stability of BmM TDMH incubated with *M. tuberculosis* in various growth media. Western blot of TDMH-bacteria mixture probed with anti-TDMH antibody after 0, 1, 3, and 7 days of incubations in: A, DMEM with 0.05% Tw (DMEMTw) or DMEMTw with fetal calf serum (FCS), B, 7H9Tween or 7H90ADCTween, and C, PBSTween or Sauton's media with Tween. Purified TDMH was loaded as a marker (M) in each blot.
Figure 10B:
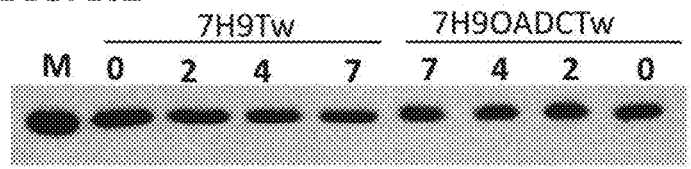
Figure 10C:
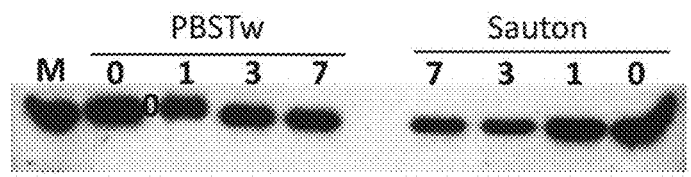

TDMH activity was evaluated in the complex chemical environments provided by several mycobacterial growth media (7H9OADC and Sauton's) and by eukaryotic cell medium (DMEM supplemented with 10% Fetal Calf Serum). TDMH activity varied widely, from the highest in Sauton's media to the lowest in 7H9OADC and DMEM-FCS (FIG. 1B), although the integrity of the enzyme remained unchanged and no protein degradation was observed under these conditions (FIG. 10). Removal of the albumin-based supplement restored TDMH activity in 7H9 and DMEM base, but not to the levels observed in Sauton's media (FIG. 1B). Because the activity in Sauton's media was even higher than in PBS, it was hypothesized that one or more components of Sauton's media could potentially enhance the enzyme activity. The most distinguishable component of Sauton's media was the 26 mM L-Asparagine (L-Asn). It was therefore tested if 26 mM L-Asn in PBST has any effect on TDMH activity. Surprisingly, an equivalent amount of L-Asn increases TDMH efficacy by 100-fold, consistent with the enhanced activity of the enzyme in Sauton's media. However, it remains unclear whether the influence of the amino acid is through its interaction with the enzyme or the bacteria. To exclude the influence of Tween-80, which can influence the properties of the mycobacterial envelope, TDMH was spotted on a lawn of *M. tuberculosis* on a detergent-free Sauton's media agar plate. An unambiguous zone of clearance around the spotted area was observed after three weeks of incubation (FIG. 1D). Thus, exposure to TDMH causes a very rapid and efficient loss of *M. tuberculosis* viability in diverse in vitro conditions.

Example 3

Viability Loss is Due to Compromised Envelope Integrity and Cellular Lysis

The most likely explanation for loss of viability in TDMH-exposed bacteria is a breach of the envelope integrity, and a subsequent bacterial lysis caused by the hydrolysis of target molecules. Lysis was indeed evidenced by the clearance of a turbid suspension of *M. tuberculosis* after exposure to 8 µM of TDMH for 48 hours (FIG. 2A). Lysis was further confirmed by the release of ATP from TDMH-exposed mc²7000 (FIG. 2B). The timing of ATP release in FIG. 2B was also consistent with the loss of cell viability at this density (FIG. 9). The integrity of the TDMH-treated bacteria was examined at the ultrastructural level by freeze-substitution electron microscopy. As expected, a distinct multi-layered architecture of the envelope, including an outer layer, was observed in the untreated bacteria (FIG. 2C, i-iii). In the TDMH-exposed bacilli, the outer layer was visibly ablated at several places (FIG. 2C, iv-viii). Cells could be captured that were either in the process of losing the cytoplasmic content during lysis (FIG. 2C, v to vii), or had completely lost the cellular content and the outer cell envelope (FIG. 2C, viii). Overall, these observations are fully consistent with the idea that exposure to TDMH breaches the integrity of the outer layer of cell envelope, thereby triggering bacterial lysis. The TDMH-dependent lysis through exogenous disruption of the envelope implies that the anti-mycobacterial activity of the enzyme will be fairly non-responsive to the physiological state of the target bacilli. This was indeed supported by a highly similar susceptibility of exponentially growing and stationary phase bacilli to TDMH exposure (FIG. 2D).

Example 4

Lysis is Associated with TDM Hydrolysis and Requires Catalytic Activity of TDMH

Figure 3A:
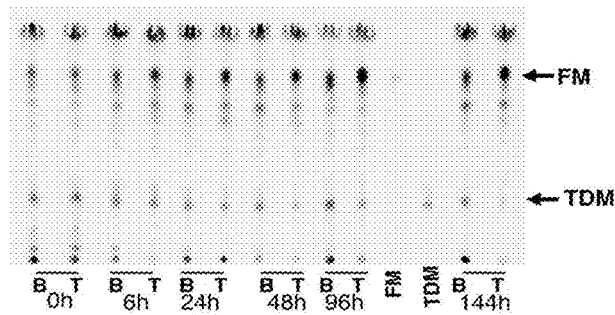
FIGS. 3A-3F. Lysis of *M. tuberculosis* is associated with TDM hydrolysis. A. Radio-thin layer chromatography (radio-TLC) of the lipids in cell-TDMH mixture (marked as T) incubated for specified hours (marked under each lane). Purified $^{14}$C-FM and $^{14}$C-TDM were loaded as markers. In the parallel control experiment, the cells were mixed with the storage buffer (marked as B) and processed similarly. B. Radio-TLC of lipids of the cell-TDMH mixtures or cells in storage buffer incubated for shorter time (marked under each lane). Purified $^{14}$C-TDM and $^{14}$C-TMM were loaded as markers (M). C. Radio-TLC of the same sample in apolar solvent to reveal FM and TDM along with their respective markers. D. Radio-TLC showing FM release when 5 µg of TDMH is incubated with TDM but not with TMM. E. Loss of in vitro hydrolytic activity in the catalytic serine mutant of TDMH (S124A) was determined by its failure to release FM when incubated with $^{14}$C-TDM in the assay buffer. Parallel reactions of $^{14}$C-TDM with wild-type TDMH or assay buffer were positive and negative controls, respectively. Purified $^{14}$C-FM was used as a marker. F. Viability of $10^7$ cfu/mL suspension of *M. tuberculosis* (H37Rv) exposed to 8 µM of TDMH (S124A). Exposures to wild-type TDMH, and storage buffer were used as parallel positive and negative controls, respectively. The error bars in panel F represent the standard errors of three independent experiments. Densitometric analysis of TDM, FM and TMM in panels A and B are provided in FIG. 11.
Figure 3B:
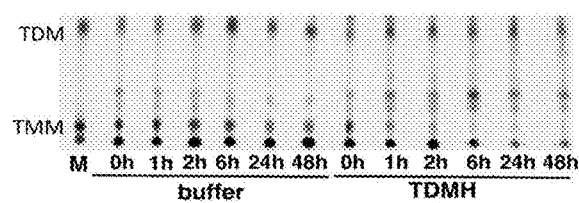
Figure 3C:
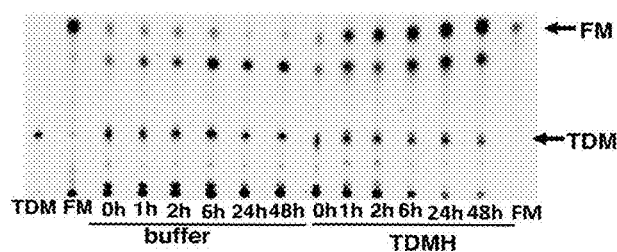
Figure 3D:
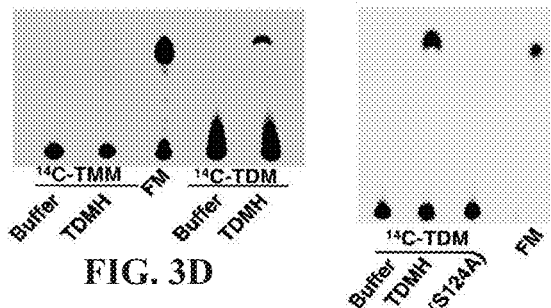
Figure 11A:
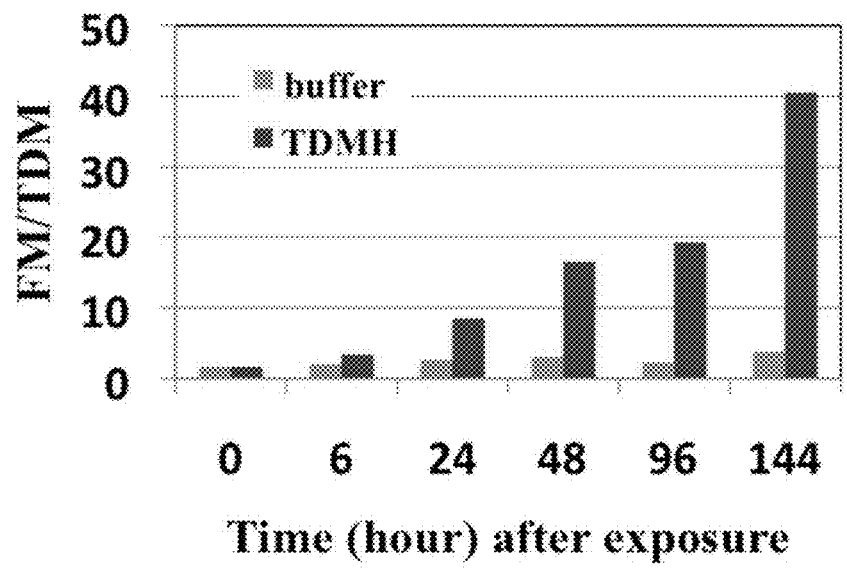
FIGS. 11A-11B are two bar graphs.
Figure 11B:
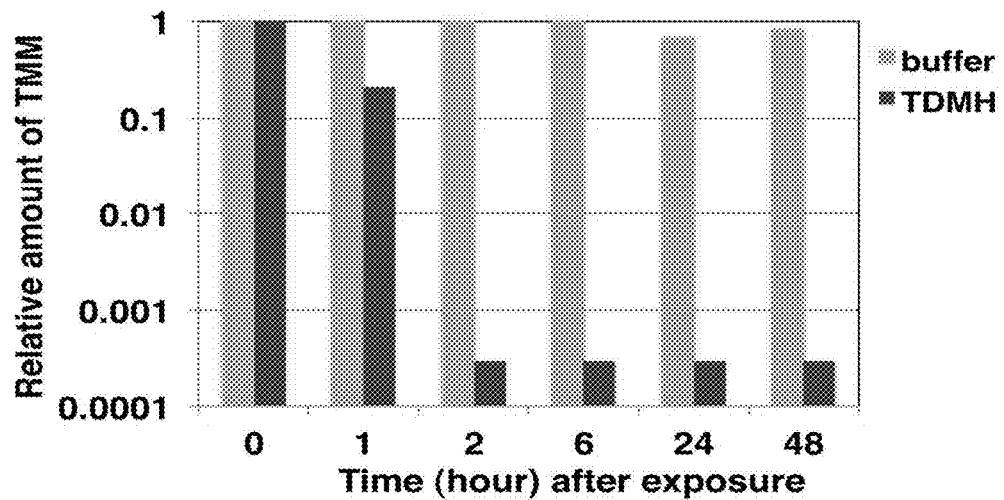

To confirm that the lysis of TDMH-exposed cells strictly relies on the enzymatic activity of the esterase, the levels of TDM and its hydrolytic product, free mycolic acids (FM), were examined in TDMH exposed *M. tuberculosis*. A higher cell density ($10^9$ cfu/mL) was used to obtain sufficient lipids in a small volume with an effective concentration (8 µM) of TDMH. Because lysis is slowed at this cell density (FIG. 9), the reactions were followed for an extended period of six days. The FM/TDM ratio in the TDMH exposed population progressively increased from 1.7 at day-0 to 40.5 at day-6 while it remained unchanged in buffer-treated cells (FIG. 11A, FIG. 11A). Interestingly, the level of FM started to accumulate much earlier, within first six hours, than the depletion of TDM could be seen (not until 48 hours of exposure) (FIG. 3A). Moreover, there was no significant viability loss in the first six hours, whereas the viability dropped to 100-fold by 48 hours (FIG. 9). This suggested a physiological response by cells during the early period of TDMH exposure in which TDM depletion could be compensated by its elevated synthesis. Without being bound by theory, it was predicted that the immediate precursor of TDM, trehalose monomycolate (TMM), would deplete earlier than TDM (Belisle et al., Science 276: 1420-1422, 1997). FIG. 3B shows that the levels of TMM indeed started to progressively decrease within the first hour of exposure, reaching to over 90% depletion in two hours, when the TDM levels and the viability of the cells still remained unchanged (FIG. 3B, FIGS. 9 and 11B). The timing of TMM depletion was consistent with the release of FM in the samples (FIG. 3C). In contrast to TDM, TMM is not a substrate of TDMH since it could not be directly hydrolyzed by TDMH (FIG. 3D). These results indicate that TMM depletion is an indirect consequence of TDMH-mediated hydrolysis of TDM.

Figure 3E:
Figure 3F:
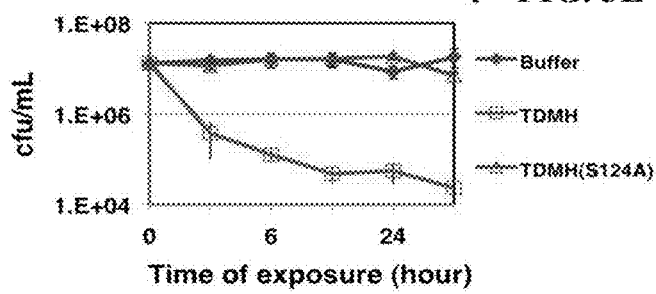

To further establish a relationship between TDM hydrolysis and bacterial lysis a point mutation was engineered in the catalytic site of TDMH, and the lytic activity of the mutant enzyme was tested. Cutinase-like serine esterases have a highly conserved catalytic triad of serine (in a GXSXG motif), aspartate and histidine (Ohja et al., supra, 2010). FIG. 3E clearly demonstrates that the TDMH(S124A) mutant failed to hydrolyze TDM, and more importantly, exposure to the mutant enzyme could not lyse *M. tuberculosis* (FIG. 3F). These results show a direct correlation between TDM hydrolysis and mycobacterial lysis.

Example 5

TDM is the Primary Target of TDMH During Lysis

Figure 4A:
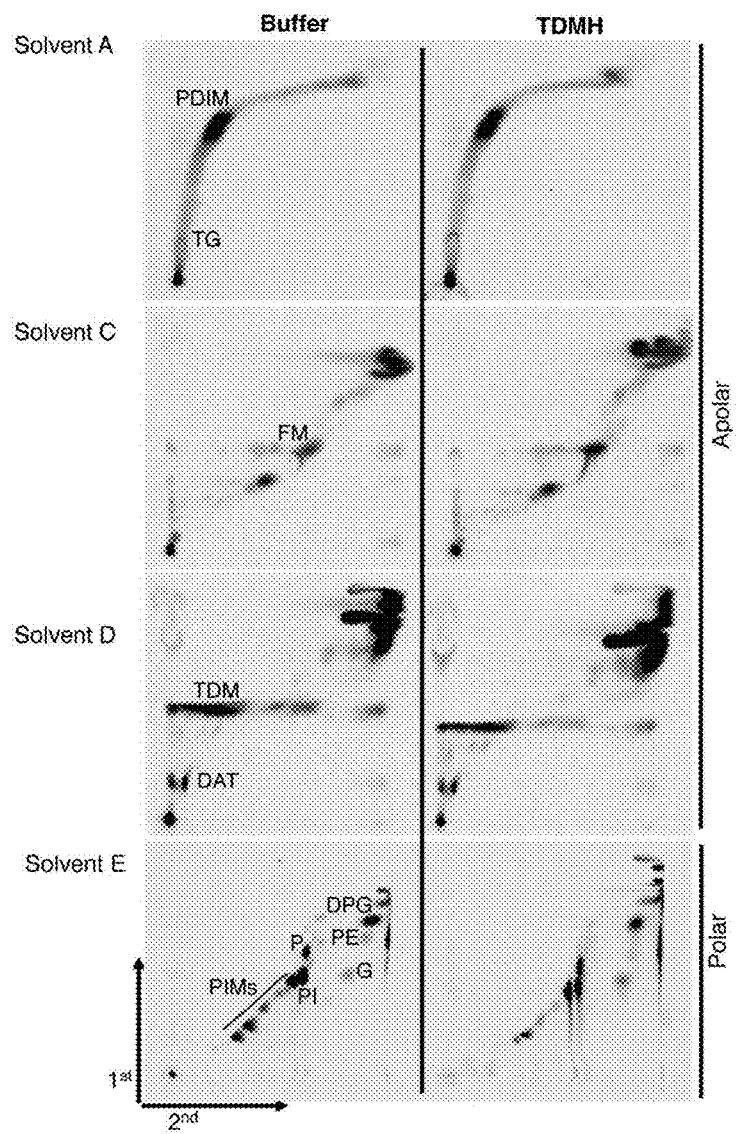
FIGS. 4A-4D. TDM is the primary target of TDMH. A. Two-dimensional radio-TLC of total apolar and polar lipids equivalent to 35000 cpm extracted from either buffer or TDMH treated cells. Apolar lipids were resolved in solvent systems A, C and D, polar lipids were resolved in solvent system E described previously (Ojha et al., PloS one 6: e25078, 2008). Positions of PDIM (Phthiocerol dimycocerosic acid), TG (triacylglyceride), DAT (2,3 di-O-acyltrehaloses), PIMs (phosphatidyl-myo-innositol mannosides), PI (phosphatidyl innositol), PE (phosphatidyl ethanolamine (PE), DPG (diphosphoatidyl glycerol), other phospholipids (P), are marked based on published reference (Besra, Preparations of cell wall fractions from *mycobacteria*. In: Parish T, Stoker N G, editors. *Mycobacteria* Protocols. Totowa, N.J.: Humana Press. pp. 91-107, 1998). Positions of TDM and FM are marked based on the migratory pattern of purified reference standards. B. Radio-TLC of lipids produced after incubation of PIM$_2$ with 5 µg of TDMH or equivalent amount of storage buffer, or with TDMH(S124A). $^{14}$C-palmitic acid (PA), Fatty acids (FA) and lyso-PIM are marked. C. Radio-TLC showing PIMs in lipids extracted from $10^9$ *M. tuberculosis* (mc$^2$7000) exposed to 8 µM of TDMH for various time (in hours) indicated below each lane. Equivalent number of bacilli exposed to storage buffer was used as negative controls. Purified PIMs were used as marker. D. Lytic activity of 0.8 µM TDMH against *M. tuberculosis* (H37Rv) in the presence of 100 µg of either purified TDM, apolar lipids (apL), polar lipids (pL), PIMs, or the mAGP complex. Cells incubated in storage buffer were used as a negative control. Percentage viability in each condition was calculated using negative control as reference (100%). The error bar indicates standard error from three independent experiments.
Figure 4B:
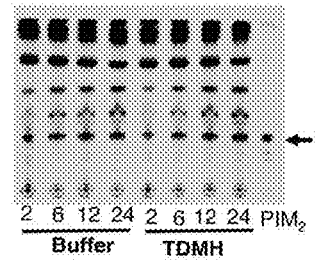

The direct (or indirect) effect of TDMH exposure on the levels of other envelope lipids was investigated. A comprehensive analysis on radio-TLC of both polar and apolar lipids from $10^9$ $^{14}$C-labeled *M. tuberculosis* treated with either buffer or 8 µM of TDMH for 48 hours, a time period when lysis is apparent under this condition, was performed. FIG. 4A shows that TDM and FM are the only major lipids among the apolar group that were altered in the TDMH-treated cells (FIG. 4A). Among the polar lipids we observed a very specific depletion of phosphotidylinnositol mannosides (PIMs) in the TDMH-treated cells (FIG. 4A). Depletion of PIMs is a direct consequence of the TDMH activity as the enzyme can hydrolyze purified PIMs into free fatty acids and lyso-PIM (FIG. 4B). The hydrolysis of PIMs by TDMH is consistent with the presence of phospholipase activity in other mycobacterial cutinase-like serine esterases (Schue et al, FASEB J 24: 1893-1903, 2010; Parker et al., J Bacteriol 189: 4153-4160, 2007).

Figure 4C:
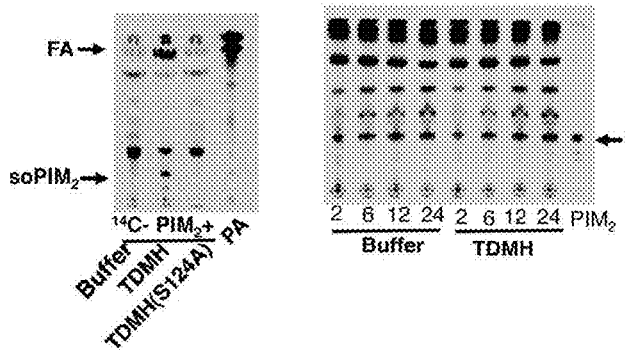

PIMs are the essential constituents of the mycobacterial envelope, localized in both the plasma membrane and the outer envelope (Ortalo-Magne et al., J Bacteriol 178: 456-461, 1996; Gilleron et al., Structure, Biosynthesis, and Activities of the Phosphatidyl-my-Inositol-Based Lipoglycans. In: Daffe M, Jean-Marc R, editors. The Mycobacterial Cell Envelope. Washington D.C.: ASM Press. pp. 75-105), 2008). PIMs are also direct precursors of lipomannan and lipoarabinomannan, which are key immunomodulary components of *M. tuberculosis* (Parker et al., J Bacteriol 189: 4153-4160, 2007). Although it is not clear as to how PIMs are organized in the outer envelope, their integration in the plasma membrane is likely through their phospholipid moieties (Gilleron et al., supra, 2008). The hydrolysis of plasma membrane PIMs is unlikely to be a pre-lysis event since compromised integrity of cell wall—a necessary prerequisite for exposure of the plasma membrane—is sufficient to cause lysis. It was investigated whether PIMs located in the outer envelope could be targeted during the pre-lysis period (first 24 hours for $10^9$ cfu/mL) of TDMH exposure. Neither the depletion of PIMs, nor the production of lyso-PIMs were observed in the TDMH-exposed $10^9$ cells during pre-lysis period (FIG. 4C), in which release of FM and depletion of TMM were observed (FIGS. 3B and C).

Figure 4D:
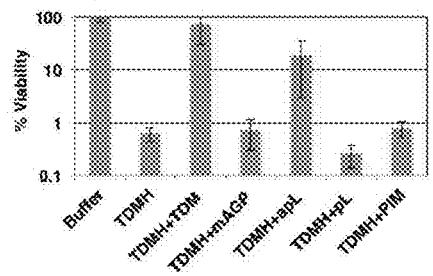

If lysis is specifically associated with TDM hydrolysis, then the lytic activity of TDMH could be competed out by an excess of purified TDM in the extracellular environment. The lytic activity of the enzyme was indeed fully inhibited in the presence of 100 µg of purified TDM in the reaction mixture (FIG. 4D). The inhibition was partial (10-fold less) with 100 µg of TDM containing apolar lipids (FIG. 4D). Importantly, 100 µg of either purified mAGP, or the PIMs containing polar lipid, or purified PIMs (~2-fold molar excess in comparison to TDM) failed to restore the viability of TDMH-treated bacteria (FIG. 4D). The failure of mAGP to inhibit the lytic activity is fully consistent with the inability of the enzyme to hydrolyze mAGP (Ohja et al., supra, 2008). Thus, TDM hydrolysis by TDMH is the primary event that triggers the lysis of *M. tuberculosis*. The PIM hydrolysis likely occurs inconsequentially, later in the lytic process.

Example 6

Limited Extractability of TDM in Petroleum Ether

Figure 5A:
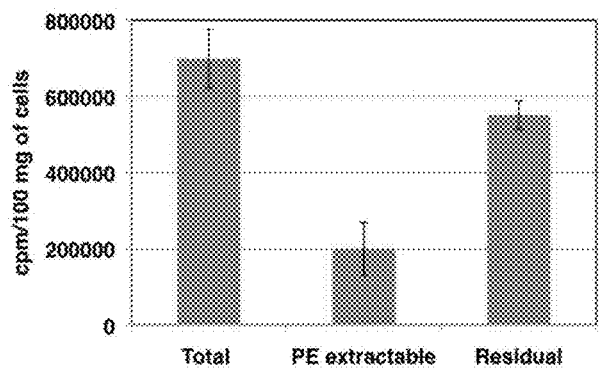
FIGS. 5A-5C. Limited extractability of TDM in petroleum ether. A. Total radio lipids (counts per minutes) extracted from 100 mg of $^{14}$C-labeled cells in either three sequential cycles of sonication in chloroform:methanol (total), or petroleum ether (PE extractable) followed by re-extraction through three cycles in chloroform:methanol (residual). B. Radio-TLC of lipids equivalent of 8000 cpm showing the levels in each of the three samples described in panel A. C. Percentage of TDM in ether extracted and residual lipids with respect to the total lipids. The values were determined by calculating the total number of TDM equivalent pixels in each of the samples obtained through densitometric analysis of TLC. The error bars in panels A and C represent standard errors of three independent experiments.
Figure 5B:
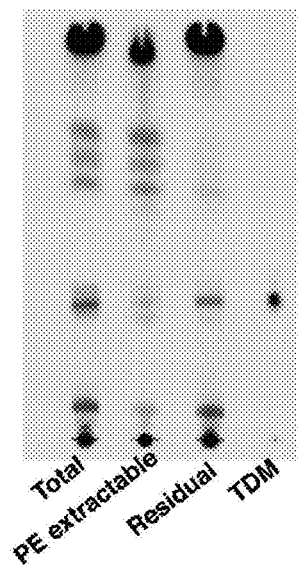
Figure 5C:
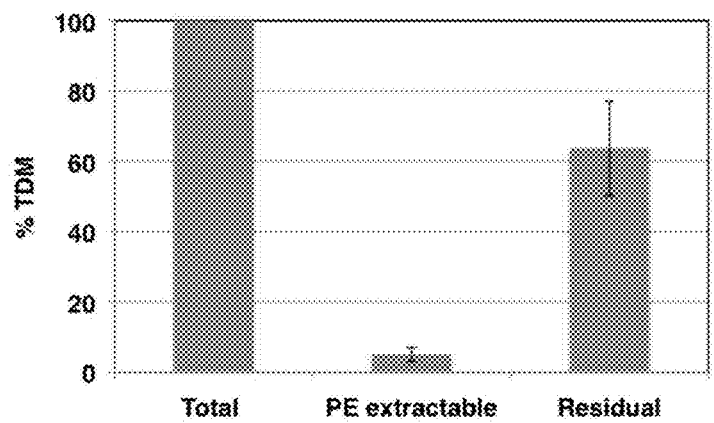

The detrimental consequence of TDM hydrolysis challenges a long-standing notion that TDM depletion by petroleum ether can be tolerated by *mycobacteria* (Bloch, J Exp Med 91: 197-218, 1950; Noll et al., Biochim Biophys Acta 20: 299-309, 1956). However, it was unclear in these studies as to what extent the total cell envelope associated TDM was extractable in this organic solvent. To this aim, the relative amounts of ether extractable and the residual TDM as a percentage of total TDM was determined. The total and residual TDM were extracted by three cycles of sonication in chloroform:methanol, whereas the ether extraction was performed by three sequential extractions in excess of the solvent. Only about 28% of the total lipids were extractable in petroleum ether (FIG. 5A). Moreover, re-extraction of residual lipids from ether-treated cells yielded over 70% of the total lipids (FIG. 5A). This reasonably validates the method of analysis. Densitometric analysis of TDM levels resolved by radio-TLC showed that the ether extracted fraction contained an average of about 5% of the TDM present in the total lipid mixture, while over 60% of the glycolipid were re-extracted in the residual lipids of the ether treated bacteria (FIGS. 5B and C). Thus, only a very limited amount of TDM is extractable in petroleum ether. It is noteworthy that extractability of TDM in an organic solvent is remarkably improved by the addition of 0.3% NaCl, and methanol to petroleum ether at a ratio of 0.1:1:1.5, but this solvent also renders the cell non-viable (data not shown). This method of apolar lipid extraction, described by Besra and colleagues (Besra, Preparations of cell wall fractions from *mycobacteria*. In: Parish T, Stoker N G, editors. *Mycobacteria* Protocols. Totowa, N.J.: Humana Press. pp. 91-107, 1998), was used for lipid analysis in FIGS. 3 and 4 of this study.

Example 7

TDMH Exposure is Detrimental to Other Mycobacterial Species

Figure 6A:
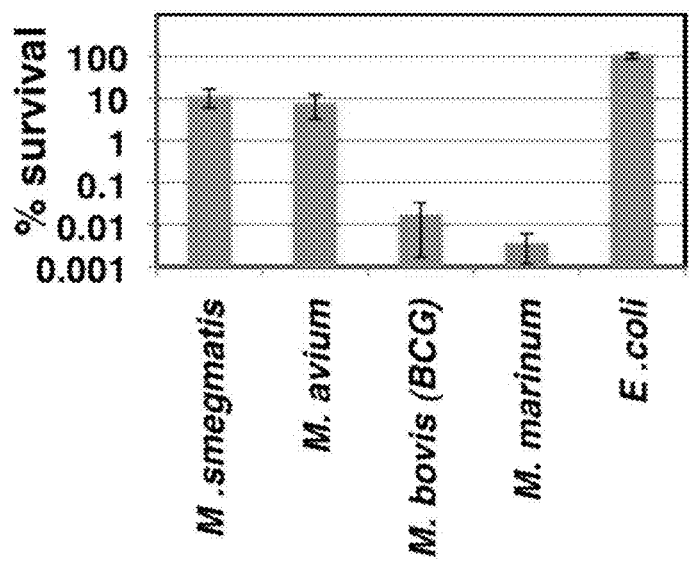
FIGS. 6A-6B. Sensitivity of multiple mycobacterial species to TDMH. A. Lytic activity of 8 µM TDMH against $10^7$ cfu/mL suspension of four other mycobacterial species and *E. coli*. The percentage survival reflects the ratio of the number of viable bacilli before and after the 48-hour exposure. B. Effect on the viability of $10^7$ cfu/mL suspension of *M. marinum* upon exposure to 8 µM TDMH (S124A) mutant. Exposure to 8 µM TDMH (wild-type), and storage buffer were positive and negative controls, respectively. The error bars in panel A and B represent standard errors of three independent experiments.
Figure 6B:
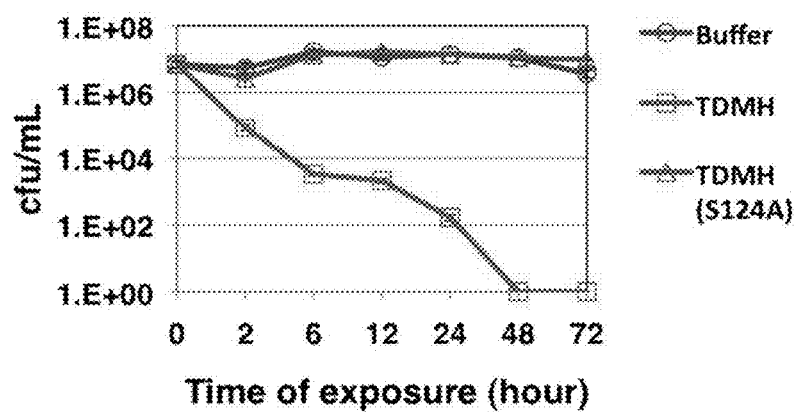

It was determined whether the exogenous TDM hydrolysis could be similarly detrimental to other mycobacterial species. The activity of TDMH against four widely studied mycobacterial species, *M. bovis* (BCG), *M. avium, M. marinum*, and *M. smegmatis*, representing both *M. tuberculosis* complex (MTC) as well as non-tuberculous *mycobacteria* (NTM) was studied. Although loss of viability was observed in all four of them, *M. smegmatis* and *M. avium* were significantly more tolerant than the other species (FIG. 6A). TDM is a unique lipid of the mycobacterial envelope, and as expected, TDMH exposure had no effect on *E. coli* viability (FIG. 6A). The decreased sensitivity of *M. smegmatis* and *M. avium* suggests that their TDM is either less exposed or recognized with a lower affinity by the enzyme. The tolerance observed in *M. smegmatis* could possibly be attributed to the fact that the enzyme is physiologically expressed by this species, and therefore may have evolved a mechanism to control the activity on its own envelope. In addition the tolerance could also originate in the distinct species of mycolates conjugated to trehalose in *M. smegmatis*—for instance presence of shorter chain α', and absence of methoxy- and keto-species (Takayama et al., Clin Microbiol Rev 18: 81-101, 2005). Interestingly, *M. marinum* appears very sensitive to TDM hydrolysis (FIG. 6A). As no account of *M. marinum* TDM was available in the literature, its presence was confirmed by structural analysis. A combined analysis of purified TDM by mass spectrometry and $^1$H-NMR spectroscopy demonstrated that TDM in *M. marinum* was substituted by a mixture of alpha-, methoxy- and keto-mycolates with sizes ranging from 74 to 87 carbons, in agreement with the total mycolates content of *M. marinum* (Watanabe et al., Microbiology 148: 1881-1902, 2002). The failure of TDMH(S124A) to lyse *M. marinum* cells (FIG. 6B) suggests that TDM hydrolysis could be the likely trigger of lysis in this species as well.

Example 8

Application of TDMH in *M. tuberculosis* Detection

Figure 7A:
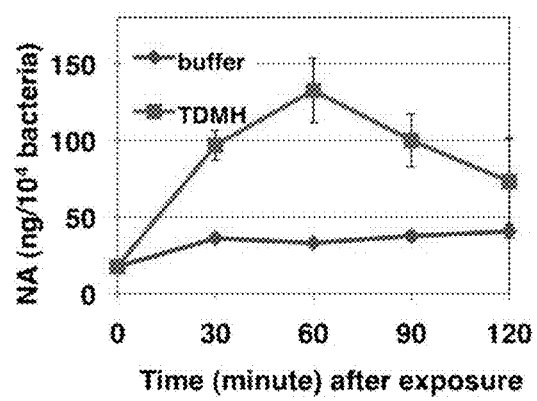
FIGS. 7A-7C. A sensitive detection of *M. tuberculosis* (Erdman) by TDMH treatment coupled with reverse transcriptase polymerase chain reaction (RT-PCR). A. Nucleic acids (NA) present in the TDMH-cell mixture measured at various time intervals. Equal volume of enzyme storage buffer was added in the cell suspension as a negative control. The error bars represent standard errors of three independent experiments. B. Amplification of 209 base pairs (bp) 16S-rRNA-specific product from DNA obtained after treatment of $10^3$, $10^2$ or 10 *M. tuberculosis* bacilli with either TDMH, or storage buffer (also see FIG. 12). A no-template control (NTC) was set up similarly, except that TDMH was incubated with PBSTA without any bacilli. A template positive control (TC) contained 0.5 ng of purified genomic DNA of *M. tuberculosis* along with the equivalent amount of TDMH in the amplification reaction. The amplification was carried out with *M. tuberculosis* specific 16S-rRNA primers and a corresponding molecular beacon probe as described earlier (E1-Hajj et al., J Clin Microbiol 39: 4131-4137, 2001). C. Amplification plot of RT-PCR for 16S-rRNA specific DNA obtained from the treatment of 10 *M. tuberculosis* bacilli with either buffer or TDMH, as described in panel B. The controls, NTC and TC, are as described in panel B.
Figure 7B:
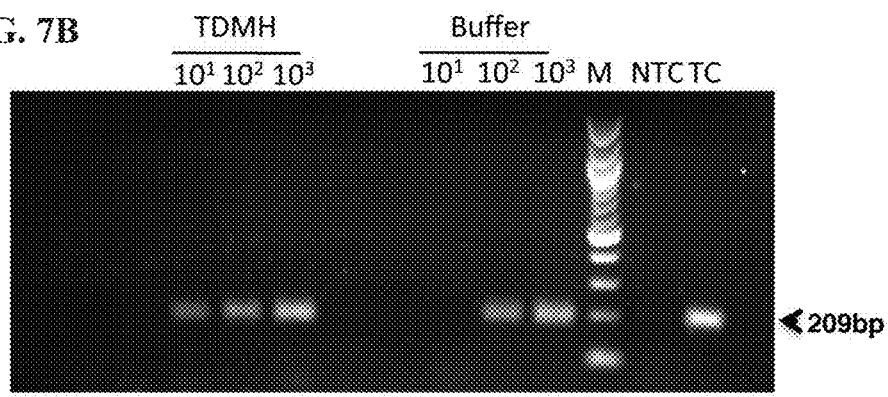
Figure 7C:
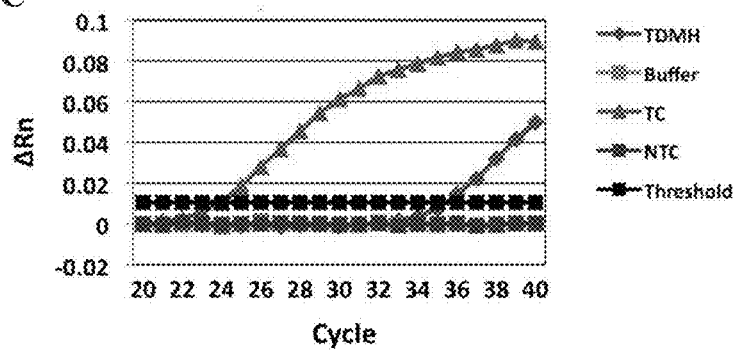
Figure 8A:
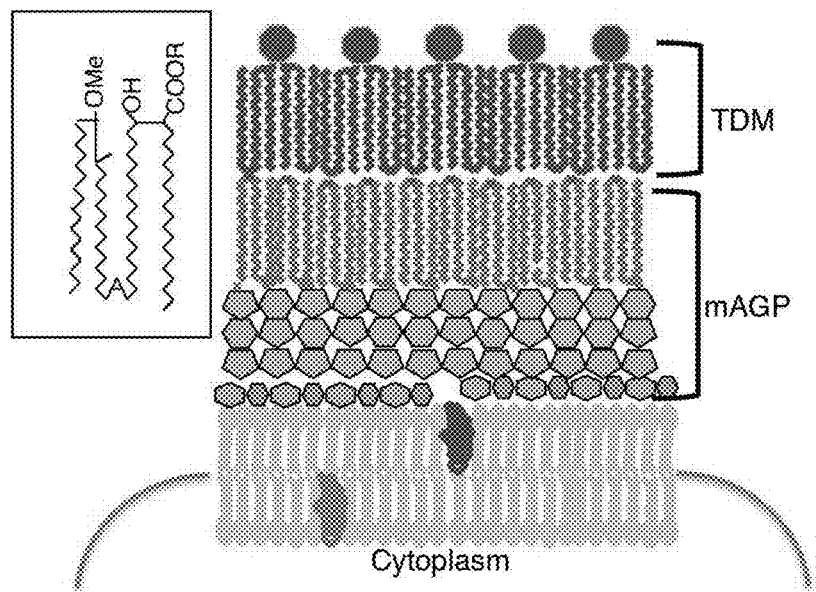
FIGS. 8A and 8B. Schematic models of TDM organization in bilayer structure of mycobacterial outer membrane with either folded (A), or extended (B) conformation of mycolic acids. The structures of mycolic acids in both conformations are shown in the insets of the respective panels.
Figure 8B:
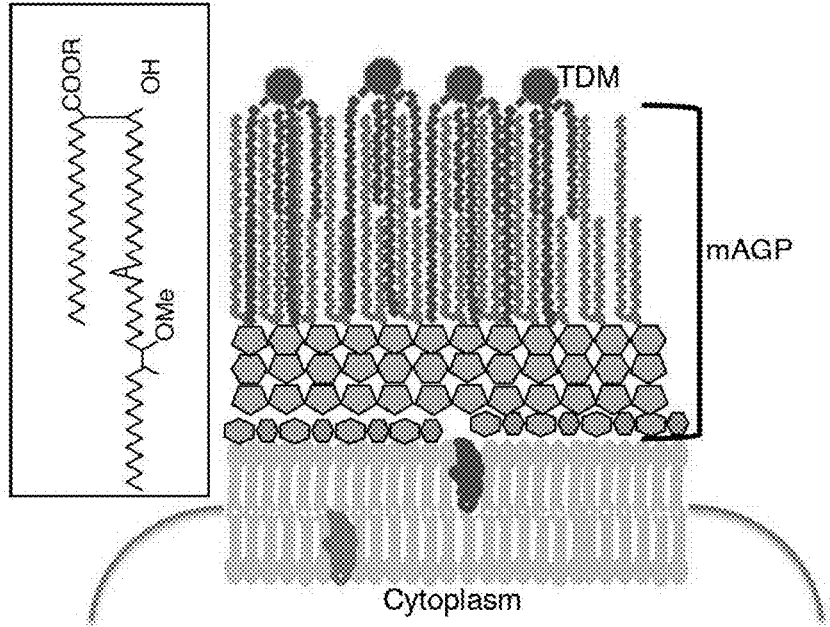
Figure 12A:
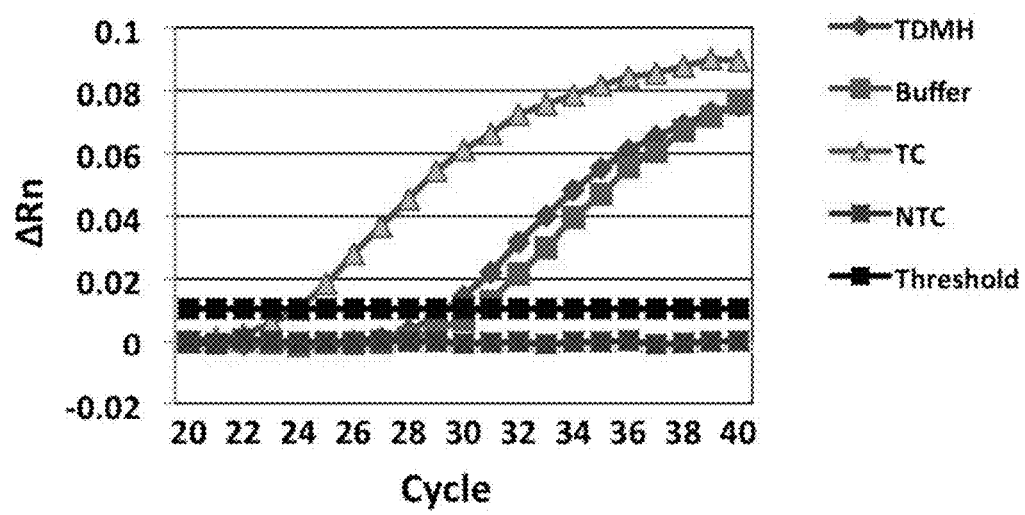
FIGS. 12A-12B are line graphs of profiles of RT-PCR with DNA from 103 (A), 102 (B) *M. tuberculosis* bacilli obtained after treatment with either TDMH, or storage buffer. A no-template control (NTC) was set up similarly except that TDMH was incubated with PBSTA without any bacilli. A template control (TC) contained 0.5 ng of purified genomic DNA along with the equivalent amount of TDMH in the amplification reaction. The amplification was carried out with *M. tuberculosis* specific 16S-rRNA primers and a corresponding molecular beacon probe as described in FIG. 7.
Figure 12B:
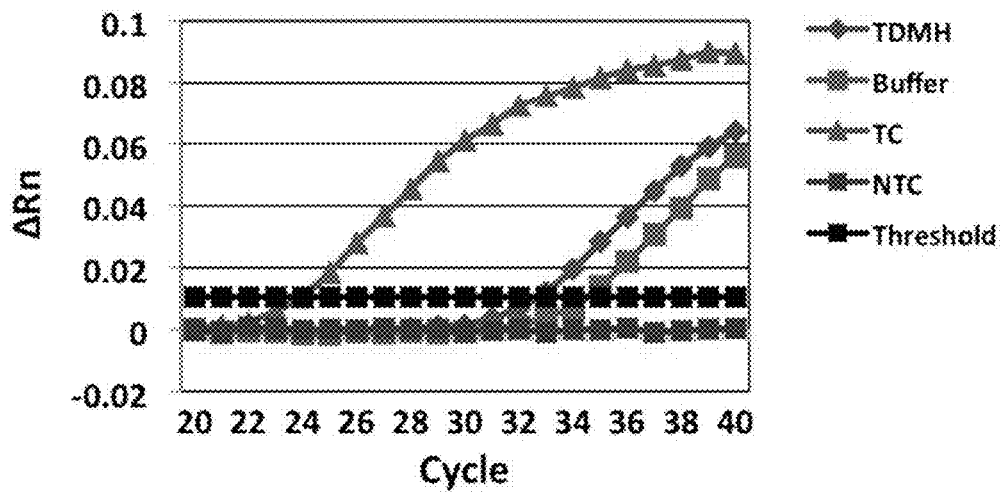
Figure 13:
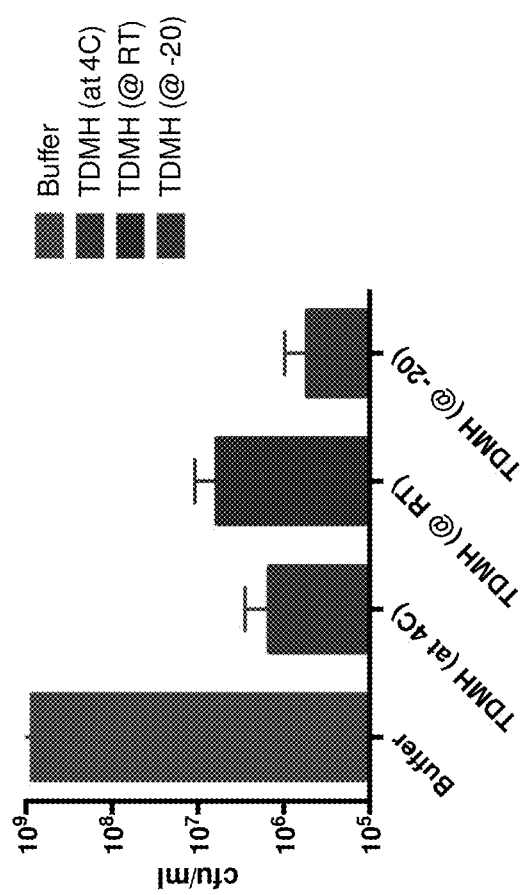
FIG. 13 is a bar graph showing that TDMH can be stored at room temperature, 4° C. or 20° C. and retain activity.

A rapid and efficient lysis of TDMH-exposed *M. tuberculosis* and subsequent release of nucleic acids (NA) can potentially be exploited for enhancing the sensitivity of PCR-based detection of the pathogen. NA content in the supernatant of TDMH exposed cells indeed started to increase within 30 minutes of exposure, and peaked at around 60 minutes (FIG. 7A). A prolonged exposure however decreased the NA content, presumably because of the activity of cellular nucleases released in the lysates. Interestingly, a cell suspension treated with the storage buffer had low but detectable amounts of NA that remained unchanged during the exposure time (FIG. 7A). An amplification of the coding region of *M tuberculosis*-specific 16S-rRNA was performed in a molecular beacon based Real time-PCR reaction, developed for TB diagnosis (E1-Hajj et al., supra, 2001). TDMH treatment had no significant advantage over the untreated control in amplifying DNA from about 100 or more bacilli (FIG. 7B and FIG. 12), presumably because of the presence of sufficient amounts of DNA in the control due to spontaneous lysis. However, the enzyme-dependent lysis was critically useful in detecting DNA from fewer bacilli (approximately 10), as there was no detectable amplification in the untreated control (FIGS. 7B and C). Thus, pretreatment of *M. tuberculosis* with TDMH can clearly facilitate an efficient extraction and sensitive detection of its DNA. This is highly relevant in the context of recent inclusion of the nucleic acid amplification (NAA) assay in the diagnostic algorithm of TB (CDC (2009) Updated guidelines for the use of nucleic acid amplification tests in the diagnosis of tuberculosis. MMWR Morb Mortal Wkly Rep 58: 7-10).

Example 9

Additional Materials and Methods

Transformation Protocol:

50 ul of competent *E. coli* cells were taken from −80° C. freezer and 1 ul of plasmid was added and mixed very gently. This was then placed in a 42° C. water bath for one minute, after which, it was placed back on ice for two minutes. This temperature shock enabled the plasmid to enter the *E. coli*, by disrupting the membrane. Following this, 1 ml of LB broth was added and placed on a shaker for 1 hour at 37° C. Next, it was spun down at 5K rpm for five minutes; 800 ul were removed and the pellet was resuspended in the remaining liquid. The cells were then plated out on LB+CB agar plates for 12 to 18 hrs. Carbenicillin, CB, is a bacteriolytic antibiotic used for selection. Only those colonies that are resistant to the antibiotic will remain, and those colonies are the ones that contain the plasmid. After, the colonies were scraped and placed in 2 ml LB broth and placed on 37° C. shaker overnight.

The next day the sample was transferred to a flask containing one liter of LB broth and 1 ml CB and placed on 37° C. shaker for three to four hours or until the optical density, o.d., read 0.6 to 0.8. After, IPTG was added (for 0.24 grams of IPTG in 1 ml) and placed on 30° C. shaker at 160 rpm for 3 hours. The cells were spun down in four different bottles at 10K rpm for five minutes at 4° C. and the supernatant was removed. After this, 10 ml lysis buffer+100 ul imidazole were added to the cell pellet and resuspended and placed on ice for 30 minutes then sonicated 10 times. The sonication process entailed 10 seconds of sonication then 20 seconds on ice. After this the samples were spun down at 1200 rpm for 30 minutes at 4° C. While the samples were being spun the agarose that would be later used was made. It involved combining 2 ml agarose and 10 ml binding buffer and this was washed 3 times. The final time the supernatant was removed and just the agarose remained.

The supernatant of the sonicated cells that were spun down for 30 minutes was added to the agarose and resuspended and put on a rotary at 4° C. for one hour after which the sample was spun down at 4° C. for five minutes at 2000 rpm and washed five times with 5 ml of wash buffer. The final time, the pellet was resuspended in 4 ml of wash buffer. This product was then transferred to a column and placed over a glass tube to let it run through and the elution buffer was added in 500 ul increments and let run through in separate microcentrifuge tubes seven times. The elution is done by $Ni^{2+}$ chromatography; in which, the protein is His-tagged which binds to the beads and allows the rest to flow through. The protein is then eluted our by using imidazole containing elution buffer to release it from the beads. A SDS PAGE gel was run and three lanes were chosen that had the most heavily concentrated bands and those were used for the dialysis.

Dialysis:

Dialysis is a method used to concentrate the enzyme in glycerol. A spectra/por dialysis reservoir was filled with a large volume of the appropriate dialysis buffer. The dialysate volume was 100 times the sample volume. (Example: 10 ml sample→1 L of dialysate). The reservoir was a larger 2 L beaker. Following this, the dialysis tubing was cut into appropriate lengths; the closure was opened. The tubing was then inserted into the opened closure and re-clamped with approximately 3 to 5 mm extending from the closure. After this, the sample was loaded into the dialysis tubing through the open end and adjusted for length. The tubing was clamped perpendicular to the previous with the second closure. Next, the dialysis sample was placed in the appropriate dialysis buffer and a clean magnetic stir bar was dropped into the dialysis reservoir and placed at 4° C. overnight. The next day it was transferred to a fresh centrifuge tube and immediately stored at −20° C.

The concentration of the enzyme was determined by using a spectrophotometer set at 260 nm. Standards using BSA were measured by the spectrophotometer and plotted to develop a trendline and subsequent equation to determine the concentration of the measured sample.

Plating rTDMH on 7H11 Agar Plates in Comparison to Standard Control of Storage Buffer:

50 ug of rTDMH were added to $10^7$ $mc^2$ 7000 bacteria, and stored overnight at 37° C. and the following day serial dilutions were made. Corresponding volume of storage buffer was added to another set of $10^8$ $mc^2$ 7000 cells as a comparison. 10 ul of each dilution was plated out on 7H11 agar plate and left for two weeks in a 37° C. incubator.

Protocol for Genomic DNA Preparation and Isolation Using rTDMH:

The stock concentration of rTDMH used was 13 ug/ul. $10^9$ cells were taken and washed with 10 ml PBS and resuspended in a microfuge tube in 1 ml of PBS-asparagine (PBS-A). PBS-A was used as it was determined to be the optimal buffer for rTDMH in comparison to PBS, PBS-tween, and NaCl. 20 ul or 260 ug of rTDMH was added to one microfuge tube and placed on a rotator for two hours at 37° C. In a corresponding tube, 20 ul of storage buffer was added to $10^9$ cells in PBS-A as a standard control.

After two hours, 100 ul of 10% sodium dodecyl sulfate (SDS) was added and mixed gently after which 10 ul of 50 mg/ml proteinase K was added, gently mixed, and placed at 55° C. for 30 minutes. Following this, 200 ul of 5M NaCl was added and gently mixed. NaCl blocks the binding of DNA to centrimide, which is present in the CTAB solution. At this point, the CTAB was preheated at 65° C. and then 160 ul of it was added to the sample, gently mixed and placed at 65° C. for 10 minutes. An equal volume of Chloroform:isoamyl alcohol (24:1 ratio) was added and shaken gently to mix and spun for five minutes at high speed. 900 ul of the supernatant was transferred to a fresh microfuge tube and the extraction was repeated this time 800 ul of the aqueous layer was transferred to a fresh microfuge tube. To the 800 ul, 560 ul (0.7× the vol) of isopropanol was added and mixed via inversion until DNA had precipitated out of solution. Then the sample was incubated at room temperature for five minutes after which it was spun down at max speed for 10 minutes and the supernatant was removed and 1 ml of 70% Ethanol was added to wash the DNA pellet and once again was spun at max speed for five minutes. The supernatant was removed and the pellet was allowed to air dry and then covered with 50 ul of TE buffer and an electrophoresis gel was run to verify presence of DNA.

Incubating Attenuated Form of *M. tuberculosis*, $mc^2$-7000 with rTDMH and Subsequently Run RT-PCR with Sample Incubation Protocol Incubation Protocol:

First $10^9$ cells were attained. 1 ml of growing culture was taken and the optical density (o.d.) was measured. An o.d. of 4 means $10^9$ cells. To achieve $10^9$ bacteria, 4 was divided by the measured, o.d.

Example:o.d.=$x$→4/$x$=#ml needed to reach $10^9$ cells

The cells were subsequently spun down at 5K rpm for 10 minutes and the supernatant was discarded. The cells were resuspended in 10 ml of PBS (to wash cells), and spun again at 5K rpm for 10 minutes. Once again the supernatant was discarded, and cells were resuspended in 1 ml PBS-Asparagine (4 g/L) and transferred to 1.5 ml microfuge tube. The desired dilutions were then made. Of the dilutions, 10 ul of each dilution was placed into a microfuge tube. 1 ul of rTDMH (or 11-17 ug) was added to each of the samples. For the non-protein control, 1 ul (or corresponding volume) of storage buffer was added to matching sample set. The samples were then incubated at 37° C. for 30 minutes. Following incubation the samples were removed and placed on a 75° C. hot plate for 20 minutes to inactivate the enzyme or any other cellular components or nucleases that could inhibit the reaction. Following this, the RT-PCR was set up.

RT-PCR Protocol:

The protocol was completed on ice and in a dimly lit room as the molecular probe is light sensitive. The RT-PCR reaction had a total volume of 10 ul. After samples were loaded to the wells and covered, the plate was wrapped in foil to protect it from light. The components of the RT-PCR are as follows:

1 ul of sample.
5 ul Applied Biosystems Taqman master mix
4 ul Millipore water
0.2 16S ul Molecular beacon probe (commercially available from Sigma-Aldrich)
0.1 ul 16SRNA primer (Forward and Reverse primer mix)

RT-PCR Conditions for Applied Biosystems master mix (Using Applied Biosystems RT-PCR machine in Dr. Alice Tarun's, PhD, lab)

95° C. 30 sec, 58° C. 1 min, 72° C. 30 sec*40 cycles

RT-PCR Samples:

The dilutions used were the following: bacteria per 10 ul RT-PCR reaction: $10^4$, $10^3$, $10^2$, 10, and 1. Data from the RT-PCR were plotted in an excel graph to compare the results between the storage buffer standard and the rTDMH treated bacteria. "NC" is negative control, "Protein" was the TDMH treated, "Buffer" was the storage buffer standard treated, and "PC" was the positive control, which consisted of purified genomic DNA.

Confirmatory Gel Electrophoresis:

The electrophoresis gel separates segments of DNA by size via a current. Because DNA is negatively charged, the DNA will "run" through the gel from the anode to the cathode. Larger pieces run slower than smaller and through this the pieces are separated by size. A standard ladder was run in one lane so that the size of the bands present in the sample could be determined. The gel that was run was a 1% Agarose gel and the components of which were as follows:

0.5 grams Standard Agarose
50 mL TBE buffer

These components are heated in a microwave for one minute, after which 0.4 ul ethidium bromide was added, mixed thoroughly and added to the gel mold. After solidified it was placed in the apparatus in TBE buffer and 5 ul of sample were added per well, with 3 ul of a 100 base pair ladder added as a standard comparison to identify the size of the DNA.

Spiking Sputum Samples with $mc^2$ 7000:

First $10^9$ cells were obtained. 1 ml of growing culture was taken and the optical density (o.d.) was measured. An o.d. of 4 meant $10^9$ cells. To achieve $10^9$ bacteria, 4 was divided by the measured, o.d. The o.d. of the bacteria used was 0.482

Example:o.d.=$x$→4/$x$=#ml needed to reach $10^9$ cells

The cells were subsequently spun down at 5K rpm for 10 minutes, and the supernatant was discarded. The cells were resuspended in 10 ml of PBS (to wash cells), and spun again at 5K rpm for 10 minutes. Once again, the supernatant was discarded and cells were resuspended in 1 ml PBS-Asparagine (4 g/L) and transferred to a 1.5 ml microfuge tube. The desired dilutions were then made. The sputum samples were spiked with the desired dilution value in 450 ul of sputum. For example, if the dilution made was $10^8$ then 50 ul was added to 450 ul of sputum to achieve a value of $10^7$ bacteria per ml of sputum. The dilutions made were $10^6$, $10^5$, $10^4$, $10^3$ per ml of sputum.

Protocol for Clarification of Sputum:

First, a decontamination fluid was made by mixing equal volumes of sterile 1M NaOH solution and 0.1M sodium citrate, and then 5 mg N-acetyl-L-cysteine was added per ml. One volume of decontamination fluid was added per volume of sputum sample and placed on shaker at 25° C. for 20 to 25 minutes, after which the samples were spun down at 12K×g for five minutes, washed with 20 mM Tris HCl and centrifuged again and the pellet was resuspended in PBS-Asparagine with 0.8× the original sputum volume.

rTDMH Incubation and RT-PCR:

The samples were treated with 11 ug (2 ul) rTDMH and a corresponding standard was treated with 2 ul of storage buffer and placed at 37° C. for 30 minutes. Following this, the samples were placed on a heat block at 75° C. for 20 minutes to inactivate the enzyme and other lysate products that could inhibit the RT-PCR. After heat inactivation the RT-PCR was set up according to the RT-PCR protocol detailed in 4.4.2 and a subsequent electrophoresis gel was run to confirm results seen in RT-PCR data.

Spiking Samples with Virulent *M. tuberculosis:*

First, $10^9$ cells were attained. 1 ml of growing culture was taken and the optical density (o.d.) was measured. An o.d. of 4 meant $10^9$ cells. To achieve $10^9$ bacteria, four was divided by the measured, o.d. The o.d. of the bacteria used was 0.61.

Example: o.d. $=x \rightarrow 4/x=$ #ml needed to reach $10^9$ cells

The cells were subsequently spun down at 5K rpm for 10 minutes and the supernatant was discarded. The cells were resuspended in 10 ml of PBS (to wash cells) and spun again at 5K rpm for 10 minutes. Once again the supernatant was discarded, and cells were resuspended in 1 ml PBS-Asparagine (4 g/L) and transferred to 1.5 ml microfuge tube. The desired dilutions were then made. The sputum samples were spiked with the desired dilution value in 450 ul of sputum. For example, if the dilution made was $10^8$, then 50 ul was added to 450 ul of sputum to achieve a value of $10^7$ bacteria per ml of sputum. The dilutions made were $10^6$, $10^5$, $10^4$, $10^3$ per ml of sputum.

Sputum Clarification:

First, a decontamination fluid was made by mixing equal volumes of sterile 1M NaOH solution and 0.1M sodium citrate, and then 5 mg N-acetyl-L-cysteine was added per ml. One volume of decontamination fluid was added per volume of sputum sample and placed on a shaker at 25° C. for 20 to 25 minutes, after which the samples were spun down at 12K×g for 5 minutes, washed with 20 mM Tris HCl and centrifuged again and the pellet was resuspended in PBS-Asparagine with 0.8× the original sputum volume.

rTDMH Treatment:

The samples were treated with 11 ug (2 ul) rTDMH and a corresponding standard was treated with 2 ul of storage buffer and placed at 37° C. for 30 minutes. Following this, the samples were placed on a heat block at 75° C. for 20 minutes to inactivate the enzyme and other lysate products that could inhibit the RT-PCR. After heat inactivation, the RT-PCR was set up according to RT-PCR protocol detailed in 4.4.2, and a subsequent electrophoresis gel was run to confirm results seen in RT-PCR data.

Example 10

RT-PCR Based Detection of *M. tuberculosis*

Detection of *M. tuberculosis* nucleic acid (NA) corresponding to 16S-rRNA in molecular beacon based RT-PCR reaction RT-PCR performed on sample with approximately 10 bacilli either treated with TDMH or storage buffer control. Controls with genomic DNA of *M. tuberculosis* as template (Template control) or without any template (NTC) contain equivalent amounts of TDMH. A summary table of threshold cycles at which signal was detected in 45 independent RT-PCR reactions from buffer and TDMH treated bacilli, (-) denotes no detectable signal. 15 independent dilutions (D1-D15) from equivalent number of broth cultures were treated in triplicates (R1-R3) with buffer or TDMH. Statistical significance between buffer and TDMH treated samples was calculated by random effect logistic regression. The results are shown in the Table below:

| | Dilutions | | | | | |
|---|---|---|---|---|---|---|
| | buffer | | | TDMH | | |
| | R1 | R2 | R3 | R1 | R2 | R3 |
| D1 | — | — | 37 | — | 38 | 35 |
| D2 | — | — | — | 35 | 37 | 36 |
| D3 | — | — | 37 | — | 36 | 37 |
| D4 | — | 38 | 37 | 37 | 37 | 37 |
| D5 | — | — | — | 37 | 37 | 37 |
| D6 | — | — | — | 38 | 38 | 38 |
| D7 | — | — | — | 37 | 36 | 38 |
| D8 | — | 35 | — | 36 | 36 | 37 |
| D9 | — | — | — | 37 | 37 | 36 |
| D10 | 39 | — | — | 37 | 36 | 38 |
| D11 | — | — | — | 36 | — | 38 |
| D12 | — | — | 37 | 34 | 37 | — |
| D13 | — | — | — | 38 | — | — |
| D14 | — | — | — | 37 | 37 | 37 |
| D15 | — | — | — | — | — | 37 |

Example 11

Storage of TDMH

The lytic activity of 8 μM TDMH stored at various temperature for four days was determined. Enzymes were stored in specified condition for four days and then added to a suspension of $10^9$ colony forming units of *M. tuberculosis* in PBC asparagine. Storage buffer was used as control. After 2 hours of incubation cells were plated on 7H11OADC to determine the number of viable bacteria. The results are shown in FIG. 13. TDMH stored at room temperature worked as well as TDMH stored at 4° C. or −20° C.

Example 12

TDMH Treatment Increases the Frequency of Positive Detection of 10-100 Mtb Bacilli in Human Sputum Two sets of human sputum were spiked with $10^6$ cfu/mL of Mtb bacilli. Both sets were clarified with NaLC—NaOH identically. Eleven independent dilutions from each set of clarified, spiked sputum was prepared to achieve 10-100 bacilli/uL of the suspension. While one set of dilution was treated with the buffer, the other set was treated with TDMH. After one hour of incubation at 37° C., 1 uL from each dilution was taken out to amplify the *Mycobacterium tuberculosis* (Mtb)-specific DNA corresponding to 16S-RNA region. Real-Time PCR was used for Amplification. The columns indicate; dilution number for buffer and TDMH treated samples and corresponding threshold cycle at which amplification was detected by the machine. No detection is marked as (-). The results are shown below:

| Dilutions | Buffer | TDMH |
| --- | --- | --- |
| D1 | 37 | 35 |
| D2 | — | 35 |
| D3 | — | 34.8 |
| D4 | — | 35.8 |
| D5 | — | 35.7 |
| D6 | — | 35.6 |
| D7 | 36.3 | 34.8 |
| D8 | — | 36 |
| D9 | — | 35.3 |
| D10 | 37 | 34.7 |
| D11 | 37.1 | 35.8 |

The results show that the addition of TDMH increased the sensitivity of the assay.

Example 13

Toxicity of TDMH in Mice

Two groups of three mice each are treated with either 1 ug or 5 ug of TDMH daily for up to 30 days. The highest dose that mouse could survive will be used for the treatment, see Example 3. The sera and tissue samples from the lungs is collected after the 30 days of protein treatment. It is determined that the protein is stable in mice. It is also determine that the mice immune system do not react against the protein.

Example 14

Effect of TDMH Treatment on *M. Tuberculosis* Infected Mice

Two groups of six mice each are infected with *M. tuberculosis* for 60 days. One group is treated daily with TDMH at the highest tolerable dose, determined from experiment 1, for 30 days. The second group is treated with placebo containing buffer in which protein is stored. After the completion of the treatment the animals are euthanized and bacterial load is determined in the placebo treated and untreated animals. A sharp decrease in bacterial load is achieved in the protein treated group as compared to the placebo group.

Thus, a broad-range anti-mycobacterial activity has been determined for TDMH. Methods for treating or preventing against a *Mycobacterium* infections are disclosed. Furthermore, TDMH can be used as a reagent to effectively lyse *mycobacteria* in clinical sample for a sensitive, convenient and consistent diagnosis of the pathogen. The compatibility of TDMH with the RT-PCR reaction can elevate the detection limit of mycobacterial DNA, and improves the sensitivity of TB diagnosis, particularly in paucibacilliary, subclinical infections or in patients co-infected with HIV. TDMH can also be exploited for rapid clearance of mycobacterial infections.

It will be apparent that the precise details of the methods or compositions described may be varied or modified without departing from the spirit of the described invention. We claim all such modifications and variations that fall within the scope and spirit of the claims below.

The invention claimed is:

1. A method of detecting *Mycobacterium* in a sample, comprising:

contacting a sample from a subject suspected of having a *Mycobacterium* infection with an effective amount of a trehalose dimycolate hydrolase comprising the amino acid sequence set forth as SEQ ID NO: 1 or SEQ ID NO: 2, wherein the trehalose dimycolate hydrolase hydrolyses trehalose, 6,6'-dimycolate to release nucleic acids comprising *Mycobacterium* RNA from the sample;

performing real-time polymerase chain reaction (PCR) on the nucleic acids comprising *Mycobacterium* RNA to amplify the *Mycobacterium* RNA into an amplified cDNA product; and detecting the amplified cDNA product, wherein the presence of the amplified cDNA product indicates the presence of *Mycobacterium* in the sample, thereby detecting the *Mycobacterium* in the sample.

2. The method of claim 1, wherein the trehalose dimycolate hydrolase consists of the amino acid sequence set forth as SEQ ID NO: 1 or SEQ ID NO: 2.

3. The method of claim 1, wherein the *Mycobacterium* is *M. tuberculosis, M. avium, M. marinum, M. bovis* (BCG), or *M. smegmatis.*

4. The method of claim 1, wherein the wherein the *Mycobacterium* is *M. tuberculosis.*

5. The method of any one of claim 1, wherein the subject has a paucibacilliary infection.

6. The method claim 1, wherein the subject is co-infected with a human immunodeficiency virus.

7. The method of claim 1, wherein the sample is a sputum sample.

8. The method of claim 1, wherein the PCR is a real-time PCR that amplifies 16S ribosomal RNA.

9. A method of detecting *Mycobacterium tuberculosis* in a sample, comprising:

contacting a sample from a subject suspected of having a *Mycobacterium tuberculosis* infection with an effective amount of a trehalose dimycolate hydrolase, wherein the trehalose dimycolate hydrolase comprises the amino acid sequence set forth as SEQ ID NO: 1 or SEQ ID NO: 2, and wherein the trehalose dimycolate hydrolase hydrolyses trehalose, 6,6'-dimycolate to release nucleic acids comprising *Mycobacterium tuberculosis* 16S ribosomal RNA from the sample;

performing real-time polymerase chain reaction on the nucleic acids comprising *Mycobacterium tuberculosis* 16S ribosomal RNA to amplify the *Mycobacterium tuberculosis* 16S ribosomal RNA into an amplified cDNA product; and detecting the amplified cDNA product, wherein the presence of the amplified cDNA product indicates the presence of *Mycobacterium tuberculosis* in the sample.

10. The method of claim 9, wherein the trehalose dimycolate consists of the amino acid sequence set forth as SEQ ID NO: 1 or SEQ ID NO: 2.

11. The method of claim 9, wherein the sample is a sputum sample.

12. The method of claim 11, further comprising clarifying the sputum sample prior to contacting the sputum sample with the trehalose dimycolate hydrolase.

13. The method of claim 12, wherein clarifying the sputum sample comprises contacting the sputum sample with sodium hydroxide, sodium citrate and N-acetyl-L-cysteine.

14. The method of claim 9, wherein the sample is contacted with the effective amount of the trehalose dimycolate hydrolase for about 30 to about 120 minutes.

15. The method of claim 9, wherein the sample is contacted with about 50 to about 500 μg of trehalose dimycolate hydrolase at about 35° C. to about 39° C.

16. The method of claim 9, wherein performing the real-time polymerase chain reaction comprises contacting the nucleic acids or the amplified cDNA with a forward and a reverse primer, wherein the forward primer comprises the nucleic acid sequence set forth as SEQ ID NO: 5 and the reverse primer comprises the nucleic acid sequence set forth as SEQ ID NO: 6.

17. The method of claim 16, wherein performing the real-time polymerase chain reaction comprises contacting the nucleic acids or the amplified cDNA with a thermostable Taq DNA polymerase.

18. The method of claim 16, wherein detecting the amplified cDNA product comprises contacting the amplified cDNA with a probe comprising the nucleic acid sequence set forth as SEQ ID NO: 7.

* * * * *

SEQUENCE LISTING

```
<160> NUMBER OF SEQ ID NOS: 7

<210> SEQ ID NO 1
<211> LENGTH: 220
<212> TYPE: PRT
<213> ORGANISM: Mycobacterium smegmatis

<400> SEQUENCE: 1

Val Ile Ser Leu Arg Lys Pro Ala Arg Leu Ala Ala Phe Ala Ser Ala
1               5                   10                  15

Val Leu Cys Ala Gly Ala Ala Leu Ala Thr Gly Pro Ala Pro Val Ala
            20                  25                  30

Ser Ala Glu Pro Cys Ser Asp Ile Glu Val Val Phe Ala Arg Gly Thr
        35                  40                  45

Ser Glu Pro Ala Gly Ile Gly Arg Val Gly Gln Ala Leu Thr Asp Ala
    50                  55                  60

Ile Arg Asn Gln Val Gly Gly Arg Thr Val Ser Thr Tyr Gly Val Asn
65                  70                  75                  80

Tyr Pro Ala Thr Tyr Asp Phe Leu Ala Ala Ala Asp Gly Ala Asn Asp
                85                  90                  95

Ala Thr Asn Arg Ile Ala Thr Leu Ala Glu Gln Cys Pro Ser Thr Arg
            100                 105                 110

Val Val Leu Gly Gly Tyr Ser Gln Gly Ala Ala Val Val Asp Met Leu
        115                 120                 125
```

```
Leu Gly Ile Pro Pro Leu Gly Asn Lys Val Gly Asn Phe Gly Ser Ala
            130                 135                 140

Pro Pro Leu Pro Ser Asn Leu Met Asn Asn Val Ala Ala Val Ala Val
145                 150                 155                 160

Phe Gly Asn Pro Ser Ala Lys Phe Gly Ile Pro Val Thr Ser Arg Phe
                165                 170                 175

Gly Gly Arg Ala Ile Asp Ala Cys Ser Asp Gly Asp Pro Ile Cys Ser
            180                 185                 190

Asp Gly Arg Asn Pro Phe Ala His Thr His Tyr Glu Ser Ser Pro Phe
        195                 200                 205

Ile Pro Gln Ala Ala Gly Leu Ile Ala Gly Leu Val
    210                 215                 220
```

<210> SEQ ID NO 2
<211> LENGTH: 225
<212> TYPE: PRT
<213> ORGANISM: Mycobacterium smegmatis

<400> SEQUENCE: 2

```
Met Thr Met Ala Ile Val Ile Ser Leu Arg Lys Pro Ala Arg Leu Ala
1               5                   10                  15

Ala Phe Ala Ser Ala Val Leu Cys Ala Gly Ala Ala Leu Ala Thr Gly
            20                  25                  30

Pro Ala Pro Val Ala Ser Ala Glu Pro Cys Ser Asp Ile Glu Val Val
        35                  40                  45

Phe Ala Arg Gly Thr Ser Glu Pro Ala Gly Ile Gly Arg Val Gly Gln
    50                  55                  60

Ala Leu Thr Asp Ala Ile Arg Asn Gln Val Gly Gly Arg Thr Val Ser
65                  70                  75                  80

Thr Tyr Gly Val Asn Tyr Pro Ala Thr Tyr Asp Phe Leu Ala Ala Ala
                85                  90                  95

Asp Gly Ala Asn Asp Ala Thr Asn Arg Ile Ala Thr Leu Ala Glu Gln
            100                 105                 110

Cys Pro Ser Thr Arg Val Val Leu Gly Gly Tyr Ser Gln Gly Ala Ala
        115                 120                 125

Val Val Asp Met Leu Leu Gly Ile Pro Pro Leu Gly Asn Lys Val Gly
    130                 135                 140

Asn Phe Gly Ser Ala Pro Pro Leu Pro Ser Asn Leu Met Asn Asn Val
145                 150                 155                 160

Ala Ala Val Ala Val Phe Gly Asn Pro Ser Ala Lys Phe Gly Ile Pro
                165                 170                 175

Val Thr Ser Arg Phe Gly Gly Arg Ala Ile Asp Ala Cys Ser Asp Gly
            180                 185                 190

Asp Pro Ile Cys Ser Asp Gly Arg Asn Pro Phe Ala His Thr His Tyr
        195                 200                 205

Glu Ser Ser Pro Phe Ile Pro Gln Ala Ala Gly Leu Ile Ala Gly Leu
    210                 215                 220

Val
225
```

<210> SEQ ID NO 3
<211> LENGTH: 663
<212> TYPE: DNA
<213> ORGANISM: Mycobacterium smegmatis

<400> SEQUENCE: 3

```
gtgatttccc tccggaagcc ggcccggttg gccgcgttcg cctcagcagt cctgtgcgcc      60
ggtgccgcgc tggccacagg ccccgccccg gtcgcctccg cagagccctg ctccgacatc     120
gaggtggtgt tcgcgcgcgg cacgagtgaa cccgccggta tcggccgcgt cggccaggcg     180
ctgaccgatg cgatccgcaa tcaggtcggt ggccgcacgg tcagcaccta cggcgtgaac     240
taccccgcca cgtacgactt cctggccgcg ccgacggcg ccaacgacgc caccaaccgc      300
atcgcgacgc tggccgagca gtgcccgtcg acgcgcgtcg tgctgggcgg ctactcgcag     360
ggcgcggccg tggtcgacat gctgctgggg atcccgcccc tgggcaacaa ggtgggcaac     420
ttcggttccg ccccgccgct gccgagcaac ctcatgaaca cgtcgcggc cgtcgcggtg      480 ttcggcaacc cgtcggccaa gttcggcatc ccggtcacca gccggttcgg cggccgcgcg     540
atcgacgcgt gcagcgacgg cgacccgatc tgttcggacg tcggaaccc gttcgcgcac      600 acgcattacg agagctcgcc gttcatcccg caggcagcag ggctgatcgc gggtctggtt     660
tag                                                                   663

<210> SEQ ID NO 4
<211> LENGTH: 5
<212> TYPE: PRT
<213> ORGANISM: Artificial Sequence
<220> FEATURE:
<223> OTHER INFORMATION: Peptide Linker

<400> SEQUENCE: 4

Gly Gly Gly Gly Ser
1               5

<210> SEQ ID NO 5
<211> LENGTH: 20
<212> TYPE: DNA
<213> ORGANISM: Artificial Sequence
<220> FEATURE:
<223> OTHER INFORMATION: Primer

<400> SEQUENCE: 5
gagatactcg agtggcgaac                                                  20

<210> SEQ ID NO 6
<211> LENGTH: 18
<212> TYPE: DNA
<213> ORGANISM: Artificial Sequence
<220> FEATURE:
<223> OTHER INFORMATION: Primer

<400> SEQUENCE: 6
ggccggctac ccgtcgtc                                                    18

<210> SEQ ID NO 7
<211> LENGTH: 32
<212> TYPE: DNA
<213> ORGANISM: Artificial Sequence
<220> FEATURE:
<223> OTHER INFORMATION: Probe

<400> SEQUENCE: 7
gcgcccgcgg cctatcagct tgttggtggc gc                                    32
```